United States Patent [19]

Niwa et al.

[11] Patent Number: 5,834,263

[45] Date of Patent: Nov. 10, 1998

[54] METHOD FOR PRODUCING 2-KETO-L-GULONIC ACID

[75] Inventors: Mineo Niwa, Muko; Yoshimasa Saito, Kawanishi; Yoshinori Ishii, Kobe; Masaru Yoshida, Aichi; Hiromi Hayashi, Nagoya, all of Japan

[73] Assignee: Fujisawa Pharmaceutical Co., Ltd., Osaka, Japan

[21] Appl. No.: 696,834

[22] PCT Filed: Feb. 24, 1995

[86] PCT No.: PCT/JP95/00285

§ 371 Date: Sep. 24, 1996

§ 102(e) Date: Sep. 24, 1996

[87] PCT Pub. No.: WO95/23220

PCT Pub. Date: Aug. 31, 1995

[30] Foreign Application Priority Data

Feb. 25, 1994 [JP] Japan ..................... 6-028612

[51] Int. Cl.[6] ............... C12P 7/60; C12N 9/04; C12N 15/00; C12N 1/00
[52] U.S. Cl. .............. 435/138; 435/190; 435/252.3; 435/320.1; 435/822; 536/23.2
[58] Field of Search ............. 435/91.2, 138, 435/147, 190, 252.3, 252.33, 320.1, 822; 536/23.2

[56] References Cited

U.S. PATENT DOCUMENTS

| | | | |
|---|---|---|---|
| 4,902,617 | 2/1990 | Fujiwara et al. | 435/138 |
| 4,916,069 | 4/1990 | Fujiwara et al. | 435/147 |
| 5,082,785 | 1/1992 | Manning et al. | 435/252.32 |
| 5,399,496 | 3/1995 | Fujiwara et al. | 435/320.1 |

OTHER PUBLICATIONS

Balbas et al. (1990) Methods in Enzymology, vol. 185, pp. 14–37.

*Primary Examiner*—Robert A. Wax
*Assistant Examiner*—Elizabeth Slobodyansky
*Attorney, Agent, or Firm*—Oblon, Spivak, McClelland, Maier & Neustadt, P.C.

[57] ABSTRACT

An expression vector containing both a DNA encoding an L-sorbose dehydrogenase and a DNA encoding an L-sorbosone dehydrogenase; a transformant having an ability to produce 2-keto-L-gulonic acid (hereinafter 2KLGA) at high yields from D-sorbitol, which is prepared by transforming, with said expression vector, a microorganism capable of producing L-sorbose at high yields from D-sorbitol, which has no or low 2KLGA-decomposing activity or a host microorganism having, in addition to the above-mentioned properties, no or low L-idonic acid-producing activity; and a process for producing 2KLGA, which comprises culturing said transformant in a medium containing D-sorbitol. According to the present invention, 2KLGA useful for the production of L-ascorbic acid can be produced with ease and in larger amounts by a single operation of culture.

10 Claims, 13 Drawing Sheets

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 530 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Gluconobacter oxydans
        ( B ) STRAIN: T-100

( i x ) FEATURE:
        ( A ) NAME/KEY: mat peptide
        ( B ) LOCATION: 1..530
        ( C ) IDENTIFICATION METHOD: experimentally ( x i ) SEQUENCE DESCRIPTION: SEQ ID NO: 1:

```
Thr Ser Gly Phe Asp Tyr Ile Val Val Gly Gly Gly Ser Ala Gly
 1               5                  10                  15

Cys Val Leu Ala Ala Arg Leu Ser Glu Asn Pro Ser Val Arg Val
                 20                  25                  30

Cys Leu Ile Glu Ala Gly Arg Arg Asp Thr His Pro Leu Ile His
                 35                  40                  45

Met Pro Val Gly Phe Ala Lys Met Thr Thr Gly Pro His Thr Trp
                 50                  55                  60

Asp Leu Leu Thr Glu Pro Gln Lys His Ala Asn Asn Arg Gln Ile
                 65                  70                  75

Pro Tyr Val Gln Gly Arg Ile Leu Gly Gly Ser Ser Ile Asn
                 80                  85                  90

Ala Glu Val Phe Thr Arg Gly His Pro Ser Asp Phe Asp Arg Trp
                 95                 100                 105

Ala Ala Glu Gly Ala Asp Gly Trp Ser Phe Arg Asp Val Gln Lys
                110                 115                 120

Tyr Phe Ile Arg Ser Glu Gly Asn Ala Val Phe Ser Gly Thr Trp
                125                 130                 135

His Gly Thr Asn Gly Pro Leu Gly Val Ser Asn Leu Ala Glu Pro
                140                 145                 150

Asn Pro Thr Ser Arg Ala Phe Val Gln Ser Cys Gln Glu Met Gly
                155                 160                 165

Leu Pro Tyr Asn Pro Asp Phe Asn Gly Ala Ser Gln Glu Gly Ala
                170                 175                 180

Gly Ile Tyr Gln Met Thr Ile Arg Asn Asn Arg Arg Cys Ser Thr
                185                 190                 195

Ala Val Gly Tyr Leu Arg Pro Ala Leu Gly Arg Lys Asn Leu Thr
                200                 205                 210

Val Val Thr Arg Ala Leu Val Leu Lys Ile Val Phe Asn Gly Thr
                215                 220                 225

Arg Ala Thr Gly Val Gln Tyr Ile Ala Asn Gly Thr Leu Asn Thr
                230                 235                 240

Ala Glu Ala Ser Gln Glu Ile Val Val Thr Ala Gly Ala Ile Gly
                245                 250                 255

Thr Pro Lys Leu Met Met Leu Ser Gly Val Gly Pro Ala Ala His
```

|     |     |     |     | 260 |     |     |     |     | 265 |     |     |     |     | 270 |
|-----|-----|-----|-----|-----|-----|-----|-----|-----|-----|-----|-----|-----|-----|-----|

Leu Arg Glu Asn Gly Ile Pro Val Val Gln Asp Leu Pro Gly Val
                275                     280                     285

Gly Glu Asn Leu Gln Asp His Phe Gly Val Asp Ile Val Ala Glu
                290                     295                     300

Leu Lys Thr Asp Glu Ser Phe Asp Lys Tyr Arg Lys Leu His Trp
                305                     310                     315

Met Leu Trp Ala Gly Leu Glu Tyr Thr Met Phe Arg Ser Gly Pro
                320                     325                     330

Val Ala Ser Asn Val Val Glu Gly Gly Ala Phe Trp Tyr Ser Asp
                335                     340                     345

Pro Ser Ser Gly Val Pro Asp Leu Gln Phe His Phe Leu Ala Glu
                350                     355                     360

Ala Gly Ala Glu Ala Gly Val Thr Ser Val Pro Lys Gly Ala Ser
                365                     370                     375

Gly Ile Thr Leu Asn Ser Tyr Val Leu Arg Pro Lys Ser Arg Gly
                380                     385                     390

Thr Val Arg Leu Arg Ser Ala Asp Pro Arg Val Asn Pro Met Val
                395                     400                     405

Asp Pro Asn Phe Leu Gly Asp Pro Ala Asp Leu Glu Thr Ser Ala
                410                     415                     420

Glu Gly Val Arg Leu Ser Tyr Glu Met Phe Ser Gln Pro Ser Leu
                425                     430                     435

Glu Lys His Ile Arg Lys Thr Cys Phe Phe Ser Gly Lys Gln Pro
                440                     445                     450

Thr Met Gln Met Tyr Arg Asp Tyr Ala Arg Glu His Gly Arg Thr
                455                     460                     465

Ser Tyr His Pro Thr Cys Thr Cys Lys Met Gly Arg Asp Asp Met
                470                     475                     480

Ser Val Val Asp Pro Arg Leu Lys Val His Gly Leu Glu Gly Ile
                485                     490                     495

Arg Ile Cys Asp Ser Ser Val Met Pro Ser Leu Leu Gly Ser Asn
                500                     505                     510

Thr Asn Ala Ala Thr Ile Met Ile Ser Glu Arg Ala Ala Asp Phe
                515                     520                     525

Ile Gln Gly Asn Ala
                530

(2) INFORMATION FOR SEQ ID NO: 2:

(i) SEQUENCE CHARACTERISTICS:
        (A) LENGTH: 497 amino acids
        (B) TYPE: amino acid
        (D) TOPOLOGY: linear (ii) MOLECULE TYPE: peptide (vi) ORIGINAL SOURCE:
        (A) ORGANISM: Gluconobacter oxydans
        (B) STRAIN: T-100

(ix) FEATURE:
        (A) NAME/KEY: mat peptide
        (B) LOCATION: 1..497
        (C) IDENTIFICATION METHOD: experimentally (xi) SEQUENCE DESCRIPTION: SEQ ID NO: 2:

Asn Val Val Ser Lys Thr Val Ser Leu Pro Leu Lys Pro Arg Glu
  1           5                   10                      15

| | | | | | | | | | | | | | |
|---|---|---|---|---|---|---|---|---|---|---|---|---|---|
|Phe|Gly|Phe|Phe|Ile|Asp|Gly|Glu|Trp|Arg|Ala|Gly|Lys|Asp|Phe|
| | | | |20| | | |25| | | |30| |
|Phe|Asp|Arg|Ser|Ser|Pro|Ala|His|Asp|Val|Pro|Val|Thr|Arg|Ile|
| | | |35| | | |40| | | |  |45| |
|Pro|Arg|Cys|Thr|Arg|Glu|Asp|Leu|Asp|Glu|Ala|Val|Ala|Ala|Ala|
| | | | |50| | | |55| | | | |60|
|Arg|Arg|Ala|Phe|Glu|Asn|Gly|Ser|Trp|Ala|Gly|Leu|Ala|Ala|Ala|
| | | | |65| | | |70| | | | |75|
|Asp|Arg|Ala|Ala|Val|Leu|Leu|Lys|Ala|Ala|Gly|Leu|Leu|Arg|Glu|
| | | | |80| | | |85| | | | |90|
|Arg|Arg|Asp|Asp|Ile|Ala|Tyr|Trp|Glu|Val|Leu|Glu|Asn|Gly|Lys|
| | | | |95| | | |100| | | | |105|
|Pro|Ile|Ser|Gln|Ala|Lys|Gly|Glu|Ile|Asp|His|Cys|Ile|Ala|Cys|
| | | | |110| | | |115| | | | |120|
|Phe|Glu|Met|Ala|Ala|Gly|Ala|Ala|Arg|Met|Leu|His|Gly|Asp|Thr|
| | | | |125| | | |130| | | | |135|
|Phe|Asn|Asn|Leu|Gly|Glu|Gly|Leu|Phe|Gly|Met|Val|Leu|Arg|Glu|
| | | | |140| | | |145| | | | |150|
|Pro|Ile|Gly|Val|Val|Gly|Leu|Ile|Thr|Pro|Trp|Asn|Phe|Pro|Phe|
| | | | |155| | | |160| | | | |165|
|Met|Ile|Leu|Cys|Glu|Arg|Ala|Pro|Phe|Ile|Leu|Ala|Ser|Gly|Cys|
| | | | |170| | | |175| | | | |180|
|Thr|Leu|Val|Val|Lys|Pro|Ala|Glu|Val|Thr|Ser|Ala|Thr|Thr|Leu|
| | | | |185| | | |190| | | | |195|
|Leu|Leu|Ala|Glu|Ile|Leu|Ala|Asp|Ala|Gly|Leu|Pro|Lys|Gly|Val|
| | | | |200| | | |205| | | | |210|
|Phe|Asn|Val|Val|Thr|Gly|Thr|Gly|Arg|Thr|Val|Gly|Gln|Ala|Met|
| | | | |215| | | |220| | | | |225|
|Thr|Glu|His|Gln|Asp|Ile|Asp|Met|Leu|Ser|Phe|Thr|Gly|Ser|Thr|
| | | | |230| | | |235| | | | |240|
|Gly|Val|Gly|Lys|Ser|Cys|Ile|His|Ala|Ala|Ala|Asp|Ser|Asn|Leu|
| | | | |245| | | |250| | | | |255|
|Lys|Lys|Leu|Gly|Leu|Glu|Leu|Gly|Gly|Lys|Asn|Pro|Ile|Val|Val|
| | | | |260| | | |265| | | | |270|
|Phe|Ala|Asp|Ser|Asn|Leu|Glu|Asp|Ala|Ala|Asp|Ala|Val|Ala|Phe|
| | | | |275| | | |280| | | | |285|
|Gly|Ile|Ser|Phe|Asn|Thr|Gly|Gln|Cys|Cys|Val|Ser|Ser|Ser|Arg|
| | | | |290| | | |295| | | | |300|
|Leu|Ile|Val|Glu|Arg|Ser|Val|Ala|Glu|Lys|Phe|Glu|Arg|Leu|Val|
| | | | |305| | | |310| | | | |315|
|Val|Pro|Lys|Met|Glu|Lys|Ile|Arg|Val|Gly|Asp|Pro|Phe|Asp|Pro|
| | | | |320| | | |325| | | | |330|
|Glu|Thr|Gln|Ile|Gly|Ala|Ile|Thr|Thr|Glu|Ala|Gln|Asn|Lys|Thr|
| | | | |335| | | |340| | | | |345|
|Ile|Leu|Asp|Tyr|Ile|Ala|Lys|Gly|Lys|Ala|Glu|Gly|Ala|Lys|Leu|
| | | | |350| | | |355| | | | |360|
|Leu|Cys|Gly|Gly|Gly|Ile|Val|Asp|Phe|Gly|Lys|Gly|Gln|Tyr|Ile|
| | | | |365| | | |370| | | | |375|
|Gln|Pro|Thr|Leu|Phe|Thr|Asp|Val|Lys|Pro|Ser|Met|Gly|Ile|Ala|
| | | | |380| | | |385| | | | |390|
|Arg|Asp|Glu|Ile|Phe|Gly|Pro|Val|Leu|Ala|Ser|Phe|His|Phe|Asp|
| | | | |395| | | |400| | | | |405|
|Thr|Val|Asp|Glu|Ala|Ile|Ala|Ile|Ala|Asn|Asp|Thr|Val|Tyr|Gly|
| | | | |410| | | |415| | | | |420|

| Leu | Ala | Ala | Ser | Val     | Trp | Ser | Lys | Asp     | Ile | Asp | Lys | Ala     | Leu | Ala     |
|-----|-----|-----|-----|---------|-----|-----|-----|---------|-----|-----|-----|---------|-----|---------|
|     |     |     |     | 425     |     |     |     | 430     |     |     |     |         |     | 435     |

| Val | Thr | Arg | Arg | Val     | Arg | Ala | Gly | Arg     | Phe | Trp | Val | Asn     | Thr | Ile     |
|-----|-----|-----|-----|---------|-----|-----|-----|---------|-----|-----|-----|---------|-----|---------|
|     |     |     |     | 440     |     |     |     | 445     |     |     |     |         |     | 450     |

| Met | Ser | Gly | Gly | Pro     | Glu | Thr | Pro | Leu     | Gly | Gly | Phe | Lys     | Gln | Ser     |
|     |     |     |     | 455     |     |     |     | 460     |     |     |     |         |     | 465     |

| Gly | Trp | Gly | Arg | Glu     | Ala | Gly | Leu | Tyr     | Gly | Val | Glu | Glu     | Tyr | Thr     |
|     |     |     |     | 470     |     |     |     | 475     |     |     |     |         |     | 480     |

| Gln | Ile | Lys | Ser | Val     | His | Ile | Glu | Thr     | Gly | Lys | Arg | Ser     | His | Trp     |
|     |     |     |     | 485     |     |     |     | 490     |     |     |     |         |     | 495     |

Ile Ser (2) INFORMATION FOR SEQ ID NO: 3:

(i) SEQUENCE CHARACTERISTICS:
        (A) LENGTH: 1596 base pairs
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Gluconobacter oxydans
        (B) STRAIN: T-100

(ix) FEATURE:
        (A) NAME/KEY: CDS
        (B) LOCATION: 1..1593
        (C) IDENTIFICATION METHOD: experimentally (ix) FEATURE:
        (A) NAME/KEY: mat peptide
        (B) LOCATION: 4..1593
        (C) IDENTIFICATION METHOD: experimentally (xi) SEQUENCE DESCRIPTION: SEQ ID NO: 3:

```
ATGACGAGCG GTTTTGATTA CATCGTTGTC GGTGGCGGTT CGGCTGGCTG TGTTCTCGCA      60
GCCCGCCTTT CCGAAAATCC TTCCGTCCGT GTCTGTCTCA TCGAGGCGGG CCGGCGGGAC     120
ACGCATCCCC TGATCCACAT GCCGGTCGGT TTCGCGAAGA TGACCACGGG GCCGCATACC     180
TGGGATCTTC TGACGGAGCC GCAGAAACAT GCGAACAACC GCCAGATCCC CTATGTGCAG     240
GGCCGGATTC TGGGCGGCGG ATCGTCCATC AACGCGGAAG TCTTCACGCG GGACACCCT     300
TCCGACTTCG ACCGCTGGGC GGCGGAAGGT GCGGATGGCT GGAGCTTCCG GGATGTCCAG     360
AAGTACTTCA TCCGTTCCGA AGGCAATGCC GTGTTTTCGG GCACCTGGCA TGGCACGAAC     420
GGGCCGCTCG GGGTGTCCAA CCTCGCGGAG CCGAACCCGA CCAGCCGTGC CTTCGTGCAG     480
AGCTGTCAGG AAATGGGGCT GCCCTACAAC CCTGACTTCA ACGGCGCATC GCAGGAAGGC     540
GCAGGCATCT ATCAGATGAC GATCCGCAAC AACCGGCGCT GCTCGACGGC TGTGGGGTAT     600
CTGCGTCCGG CTCTGGGGCG GAAGAACCTG ACGGTTGTGA CGCGGGCGCT GGTCCTGAAG     660
ATCGTCTTCA ACGGAACGCG GGCGACGGGC GTGCAGTATA TCGCCAACGG CACCCTGAAT     720
ACCGCCGAAG CGAGCCAGGA AATCGTTGTG ACGGCCGGAG CGATCGGAAC GCCGAAGCTG     780
ATGATGCTGT CGGGCGTCGG GCCTGCCGCG CATCTTCGCG AAAATGGTAT CCCGGTCGTG     840
CAGGATCTGC CGGGCGTGGG CGAGAACCTT CAGGATCATT TCGGTGTGGA TATCGTAGCC     900
GAGCTCAAGA CGGATGAGAG CTTCGACAAG TACCGGAAAC TGCACTGGAT GCTGTGGGCA     960
GGTCTTGAAT ATACCATGTT CAGATCCGGT CCCGTTGCAT CCAACGTGGT TGAGGGCGGC    1020
GCGTTCTGGT ACTCGGACCC GTCATCGGGT GTTCCTGATC TCCAGTTCCA TTTTCTTGCG    1080
```

| | | | | | | |
|---|---|---|---|---|---|---|
| GAGGCTGGGG | CTGAGGCTGG | AGTGACGTCC | GTTCCCAAGG | GAGCGTCCGG | GATTACGCTG | 1140 |
| AACAGCTATG | TGCTGCGTCC | GAAGTCTCGT | GGAACTGTCC | GGCTGCGTTC | GGCAGATCCA | 1200 |
| AGGGTCAATC | CGATGGTCGA | TCCCAATTTC | CTTGGAGACC | CGGCCGACCT | TGAGACGTCT | 1260 |
| GCGGAAGGTG | TGCGCCTGAG | CTACGAGATG | TTCTCCCAGC | CGTCTTTGGA | GAAGCACATC | 1320 |
| CGGAAAACCT | GTTTCTTTAG | CGGTAAACAG | CCGACGATGC | AGATGTATCG | GGACTATGCG | 1380 |
| CGGGAACATG | GCCGGACGTC | CTATCATCCG | ACATGCACCT | GCAAGATGGG | TCGTGATGAC | 1440 |
| ATGTCCGTCG | TCGATCCGCG | TCTGAAGGTT | CATGGCCTTG | AGGGCATCAG | GATCTGTGAC | 1500 |
| AGTTCGGTTA | TGCCGTCGCT | GCTCGGTTCC | AACACCAATG | CTGCGACGAT | CATGATCAGT | 1560 |
| GAGCGGGCAG | CGGATTTCAT | TCAGGGGAAC | GCCTGA | | | 1596 |

( 2 ) INFORMATION FOR SEQ ID NO: 4:

( i ) SEQUENCE CHARACTERISTICS:
        ( A ) LENGTH: 1497 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Gluconobacter oxydans
        ( B ) STRAIN: T-100

( i x ) FEATURE:
        ( A ) NAME/KEY: CDS
        ( B ) LOCATION: 1..1494
        ( C ) IDENTIFICATION METHOD: experimentally ( i x ) FEATURE:
        ( A ) NAME/KEY: mat peptide
        ( B ) LOCATION: 4..1494
        ( C ) IDENTIFICATION METHOD: experimentally ( x i ) SEQUENCE DESCRIPTION: SEQ ID NO: 4:

| | | | | | | |
|---|---|---|---|---|---|---|
| ATGAATGTTG | TCTCAAAGAC | TGTATCTTTA | CCGTTAAAGC | CGCGTGAGTT | CGGATTCTTT | 60 |
| ATTGATGGAG | AATGGCGCGC | AGGTAAGGAT | TTCTTCGATC | GTTCCTCGCC | GGCTCATGAT | 120 |
| GTTCCCGTCA | CCCGTATTCC | ACGCTGCACC | CGTGAAGACC | TTGATGAGGC | AGTCGCTGCT | 180 |
| GCACGTCGTG | CTTTCGAGAA | CGGAAGCTGG | GCGGGTCTGG | CAGCCGCGGA | TCGTGCGGCG | 240 |
| GTTCTTCTGA | AAGCCGCGGG | CCTTCTGCGC | GAGCGCCGTG | ATGACATCGC | TTACTGGGAA | 300 |
| GTTCTCGAAA | ACGGGAAGCC | CATCAGCCAG | GCGAAAGGTG | AGATCGATCA | CTGTATCGCC | 360 |
| TGTTTCGAGA | TGGCGGCCGG | CGCTGCGCGG | ATGCTGCATG | GTGATACGTT | CAACAATCTG | 420 |
| GGCGAGGGGC | TGTTTGGCAT | GGTCCTGCGG | GAGCCCATCG | GTGTCGTCGG | TCTGATTACG | 480 |
| CCGTGGAACT | TCCCGTTCAT | GATCCTGTGT | GAGCGGGCGC | CTTTCATTCT | CGCATCCGGC | 540 |
| TGCACGCTGG | TCGTCAAGCC | TGCCGAAGTC | ACGAGTGCCA | CGACCCTTCT | TCTGGCAGAA | 600 |
| ATCCTTGCCG | ATGCCGGGCT | GCCGAAGGGT | GTCTTCAATG | TCGTGACAGG | CACGGGGCGC | 660 |
| ACGGTCGGTC | AGGCCATGAC | CGAGCATCAG | GATATCGACA | TGCTGTCCTT | CACGGGCTCC | 720 |
| ACGGGCGTCG | GCAAGTCCTG | TATCCACGCG | GCGGCTGACA | GCAACCTGAA | GAAACTTGGC | 780 |
| CTCGAACTGG | GCGGCAAGAA | CCCGATTGTC | GTGTTCGCTG | ACAGCAACCT | TGAGGATGCG | 840 |
| GCCGACGCGG | TAGCCTTCGG | GATCAGCTTT | AATACCGGGC | AGTGCTGTGT | GTCGTCGAGC | 900 |
| CGCCTGATCG | TAGAGCGGTC | CGTGGCGGAG | AAGTTCGAGC | GCCTCGTCGT | GCCAAAAATG | 960 |
| GAGAAGATCC | GCGTTGGTGA | TCCGTTTGAT | CCGAAACGC | AGATTGGCGC | CATCACGACG | 1020 |

| | | | | | | |
|---|---|---|---|---|---|---|
| GAAGCGCAGA | ACAAGACCAT | TCTGGACTAT | ATCGCGAAAG | GCAAGGCCGA | GGGCGCCAAG | 1080 |
| CTGCTCTGTG | GTGGCGGGAT | CGTCGATTTC | GGCAAGGGAC | AGTATATCCA | GCCCACGCTT | 1140 |
| TTCACGGATG | TGAAGCCCTC | GATGGGCATC | GCGCGTGACG | AGATTTTTGG | GCCGGTTCTG | 1200 |
| GCGTCCTTCC | ACTTCGATAC | CGTCGATGAG | GCGATCGCGA | TTGCCAATGA | CACGGTTTAC | 1260 |
| GGCTTGGCCG | CATCGGTCTG | GAGCAAGGAT | ATCGACAAGG | CGCTTGCCGT | GACCCGTCGT | 1320 |
| GTTCGTGCCG | GCCGCTTCTG | GGTGAACACC | ATCATGAGCG | GTGGTCCCGA | GACGCCGCTG | 1380 |
| GGTGGTTTCA | AGCAGTCGGG | CTGGGGCCGT | GAGGCCGGTC | TGTACGGCGT | TGAGGAATAT | 1440 |
| ACGCAGATCA | AATCTGTCCA | TATCGAAACT | GGCAAACGTT | CGCACTGGAT | TTCGTAA | 1497 |

(2) INFORMATION FOR SEQ ID NO: 5:

(i) SEQUENCE CHARACTERISTICS:
        (A) LENGTH: 4624 base pairs
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Gluconobacter oxydans
        (B) STRAIN: T-100

(ix) FEATURE:
        (A) NAME/KEY: CDS
        (B) LOCATION: 1041..2534, 2537..4129
        (C) IDENTIFICATION METHOD: experimentally (ix) FEATURE:
        (A) NAME/KEY: mat peptide
        (B) LOCATION: 1044..2534, 2540..4129
        (C) IDENTIFICATION METHOD: experimentally (xi) SEQUENCE DESCRIPTION: SEQ ID NO: 5:

| | | | | | | |
|---|---|---|---|---|---|---|
| GAATTCAGGG | GGGTGAGATG | TATGTTTGTA | AGAAAAACTG | CGCCTTAATT | CTTGCAGACC | 60 |
| AGGCGGCATA | TCGTTTCGAT | ATTAAAGGAA | ATTCTTTCTT | CAAGCGCTTC | GGGGGCTGTA | 120 |
| AAATCCCGCT | CGAAGATTAC | CGATCCCGTG | AAGCGGTTTG | TGAAATAATA | ATAATTGATC | 180 |
| GAGGCGATCG | TGATGTTCAG | CTGGGCTGCG | TCAATGCCAT | CGCGGAAGAC | GTTTTCCCGA | 240 |
| ACCCCCCGAT | CCAGAAGAGA | CTGGATGCGG | CGGACGAATT | TCTGACTGAT | CGTCTTCAGT | 300 |
| GTGGGCGAGT | TCCGGATATG | GGCGGCCTGA | CAGAGGTTCT | CGCTGTTCAC | AAGGGTGATG | 360 |
| AACTCCGGAT | TGGCGATATA | GTATTCCCAT | GTGAAACGGA | CGAGCGTTTC | GGAGTGCTGT | 420 |
| CCTGGGGGGC | AGGTTCTCCA | GATCCAGTCT | GGTCTCTTCC | TCCCGAATGT | TGAGGTATTT | 480 |
| CCGCTCCAGG | ACGGTGCGGA | AGAGCCCGTC | CTTACTTTTG | AAGTAGTGGT | AGAGCATCCT | 540 |
| CTTGTTGGCC | TTGGCATCGA | GGGCGATCGT | ATCGACCCGC | GCGCCTTCAA | GCCCGTTTCG | 600 |
| GGCAAACTCC | TTCTTCGCCG | CTTCGAGAAT | GCGTAATTTC | GTGGCCTCAG | CGTCCCTGAC | 660 |
| ACGCTTTTTC | GTAGAGGAGG | ACGCTCTGCT | TTTCTCAAGG | GGCATCAGGG | GTTTGTTCCG | 720 |
| CTCTCAGTAG | GGGCGCTCTT | TCTGGGGGAA | ACCGCCCCAA | AAGAAAAGCG | GATCATAAAA | 780 |
| TCACACTTAA | AGTACGAAAA | AATATCAACG | TAACGTGATT | TCATGCTGGC | GTACCCTGC | 840 |
| GATATGTGTA | AGTAACTACA | CGGTGCGTTA | CGCGTCAGGA | AGTTGGAACC | CGAGCGTCTG | 900 |
| TGGTCAAATG | CAGGTGAGGG | TCGTCCGTGA | TTAAGAATTG | CATGTTGTAA | TATCTCTCGG | 960 |
| GGTTTCCAGT | TCATAAGAGT | AAAACCGGGC | TGTTCATCGG | AAAAGGGATG | GCAGCACCAT | 1020 |
| AGTCAGTAGG | AATATTTCTC | ATGAATGTTG | TCTCAAAGAC | TGTATCTTTA | CCGTTAAAGC | 1080 |
| CGCGTGAGTT | CGGATTCTTT | ATTGATGGAG | AATGGCGCGC | AGGTAAGGAT | TTCTTCGATC | 1140 |

```
GTTCCTCGCC GGCTCATGAT GTTCCCGTCA CCCGTATTCC ACGCTGCACC CGTGAAGACC    1200
TTGATGAGGC AGTCGCTGCT GCACGTCGTG CTTTCGAGAA CGGAAGCTGG GCGGGTCTGG    1260
CAGCCGCGGA TCGTGCGGCG GTTCTTCTGA AAGCCGCGGG CCTTCTGCGC GAGCGCCGTG    1320
ATGACATCGC TTACTGGGAA GTTCTCGAAA ACGGGAAGCC CATCAGCCAG GCGAAAGGTG    1380
AGATCGATCA CTGTATCGCC TGTTTCGAGA TGGCGGCCGG CGCTGCGCGG ATGCTGCATG    1440
GTGATACGTT CAACAATCTG GGCGAGGGGC TGTTTGGCAT GGTCCTGCGG GAGCCCATCG    1500
GTGTCGTCGG TCTGATTACG CCGTGGAACT TCCCGTTCAT GATCCTGTGT GAGCGGGCGC    1560
CTTTCATTCT CGCATCCGGC TGCACGCTGG TCGTCAAGCC TGCCGAAGTC ACGAGTGCCA    1620
CGACCCTTCT TCTGGCAGAA ATCCTTGCCG ATGCCGGGCT GCCGAAGGGT GTCTTCAATG    1680
TCGTGACAGG CACGGGCGC ACGGTCGGTC AGGCCATGAC CGAGCATCAG GATATCGACA    1740
TGCTGTCCTT CACGGGCTCC ACGGGCGTCG GCAAGTCCTG TATCCACGCG GCGGCTGACA    1800
GCAACCTGAA GAAACTTGGC CTCGAACTGG GCGGCAAGAA CCCGATTGTC GTGTTCGCTG    1860
ACAGCAACCT TGAGGATGCG GCCGACGCGG TAGCCTTCGG GATCAGCTTT AATACCGGGC    1920
AGTGCTGTGT GTCGTCGAGC CGCCTGATCG TAGAGCGGTC CGTGGCGGAG AAGTTCGAGC    1980
GCCTCGTCGT GCCAAAAATG GAGAAGATCC GCGTTGGTGA TCCGTTTGAT CCCGAAACGC    2040
AGATTGGCGC CATCACGACG GAAGCGCAGA ACAAGACCAT TCTGGACTAT ATCGCGAAAG    2100
GCAAGGCCGA GGGCGCCAAG CTGCTCTGTG GTGGCGGGAT CGTCGATTTC GGCAAGGGAC    2160
AGTATATCCA GCCCACGCTT TTCACGGATG TGAAGCCCTC GATGGGCATC GCGCGTGACG    2220
AGATTTTTGG GCCGGTTCTG GCGTCCTTCC ACTTCGATAC CGTCGATGAG GCGATCGCGA    2280
TTGCCAATGA CACGGTTTAC GGCTTGGCCG CATCGGTCTG GAGCAAGGAT ATCGACAAGG    2340
CGCTTGCCGT GACCCGTCGT GTTCGTGCCG GCCGCTTCTG GGTGAACACC ATCATGAGCG    2400
GTGGTCCCGA GACGCCGCTG GGTGGTTTCA AGCAGTCGGG CTGGGGCCGT GAGGCCGGTC    2460
TGTACGGCGT TGAGGAATAT ACGCAGATCA AATCTGTCCA TATCGAAACT GGCAAACGTT    2520
CGCACTGGAT TTCGTAATGA CGAGCGGTTT TGATTACATC GTTGTCGGTG GCGGTTCGGC    2580
TGGCTGTGTT CTCGCAGCCC GCCTTTCCGA AAATCCTTCC GTCCGTGTCT GTCTCATCGA    2640
GGCGGGCCGG CGGGACACGC ATCCCCTGAT CCACATGCCG GTCGGTTTCG CGAAGATGAC    2700
CACGGGGCCG CATACCTGGG ATCTTCTGAC GGAGCCGCAG AAACATGCGA ACAACCGCCA    2760
GATCCCCTAT GTGCAGGGCC GGATTCTGGG CGGCGGATCG TCCATCAACG CGGAAGTCTT    2820
CACGCGGGGA CACCCTTCCG ACTTCGACCG CTGGGCGGCG GAAGGTGCGG ATGGCTGGAG    2880
CTTCCGGGAT GTCCAGAAGT ACTTCATCCG TTCCGAAGGC AATGCCGTGT TTCGGGCAC    2940
CTGGCATGGC ACGAACGGGC CGCTCGGGGT GTCCAACCTC GCGGAGCCGA ACCCGACCAG    3000
CCGTGCCTTC GTGCAGAGCT GTCAGGAAAT GGGGCTGCCC TACAACCCTG ACTTCAACGG    3060
CGCATCGCAG GAAGGCGCAG GCATCTATCA GATGACGATC CGCAACAACC GGCGCTGCTC    3120
GACGGCTGTG GGGTATCTGC GTCCGGCTCT GGGGCGGAAG AACCTGACGG TTGTGACGCG    3180
GGCGCTGGTC CTGAAGATCG TCTTCAACGG AACGCGGGCG ACGGGCGTGC AGTATATCGC    3240
CAACGGCACC CTGAATACCG CCGAAGCGAG CCAGGAAATC GTTGTGACGG CCGGAGCGAT    3300
CGGAACGCCG AAGCTGATGA TGCTGTCGGG CGTCGGGCCT GCCGCGCATC TTCGCGAAAA    3360
TGGTATCCCG GTCGTGCAGG ATCTGCCGGG CGTGGGCGAG AACCTTCAGG ATCATTTCGG    3420
TGTGGATATC GTAGCCGAGC TCAAGACGGA TGAGAGCTTC GACAAGTACC GGAAACTGCA    3480
CTGGATGCTG TGGGCAGGTC TTGAATATAC CATGTTCAGA TCCGGTCCCG TTGCATCCAA    3540
```

| | | | | | |
|---|---|---|---|---|---|
| CGTGGTTGAG | GGCGGCGCGT | TCTGGTACTC | GGACCCGTCA | TCGGGTGTTC | CTGATCTCCA | 3600 |
| GTTCCATTTT | CTTGCGGAGG | CTGGGGCTGA | GGCTGGAGTG | ACGTCCGTTC | CCAAGGGAGC | 3660 |
| GTCCGGGATT | ACGCTGAACA | GCTATGTGCT | GCGTCCGAAG | TCTCGTGGAA | CTGTCCGGCT | 3720 |
| GCGTTCGGCA | GATCCAAGGG | TCAATCCGAT | GGTCGATCCC | AATTTCCTTG | AGACCCGGC | 3780 |
| CGACCTTGAG | ACGTCTGCGG | AAGGTGTGCG | CCTGAGCTAC | GAGATGTTCT | CCCAGCCGTC | 3840 |
| TTTGGAGAAG | CACATCCGGA | AAACCTGTTT | CTTTAGCGGT | AAACAGCCGA | CGATGCAGAT | 3900 |
| GTATCGGGAC | TATGCGCGGG | AACATGGCCG | GACGTCCTAT | CATCCGACAT | GCACCTGCAA | 3960 |
| GATGGGTCGT | GATGACATGT | CCGTCGTCGA | TCCGCGTCTG | AAGGTTCATG | GCCTTGAGGG | 4020 |
| CATCAGGATC | TGTGACAGTT | CGGTTATGCC | GTCGCTGCTC | GGTTCCAACA | CCAATGCTGC | 4080 |
| GACGATCATG | ATCAGTGAGC | GGGCAGCGGA | TTTCATTCAG | GGAACGCCT | GATCCGGGAT | 4140 |
| TTCCCCATAC | CACCTGAAAG | CGTGATCCGG | GATTTCCCCA | TACCACCTGA | AAACGCGCAA | 4200 |
| TAGCGGAAAA | GTCTTGCTGC | CATGCCGGGC | TTTTTCATTC | GAAATTATAG | TAACTAACCA | 4260 |
| GTTAGATACA | AAGGCATTGG | AAGATGACGA | AAGTCAGGAC | AGCGACCGAG | GCTGTGAGCC | 4320 |
| TCATCAGGGA | CGGAGCCATG | GTTGCCGTCA | ATTCGTCCTC | GGGGCTTCTG | TGTCCCGACG | 4380 |
| CGGTTCTTGA | AGCACTGGGA | CAGCGTTTCG | AGGCTACAAA | ATCTCCATCT | AAACTGACGA | 4440 |
| CCATCCATCC | GATTGCCGCA | GGCGACATGT | TCGGGACCAA | GGGCGTGGAC | CATCTTGCCC | 4500 |
| GTCCGGGCAT | GATTACGAAG | ATCATTGGCG | GCTCCTATCC | TTCCGGGCCG | AGCAATGCCG | 4560 |
| AGCCACCGCT | GATCTGGCAG | CGCATCCAGG | CAGAAGATCC | GACCTGCAGG | CATGCAAGCT | 4620 |
| TGGC | | | | | | 4624 |

( 2 ) INFORMATION FOR SEQ ID NO: 6:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 6:

Thr Ser Gly Phe Asp Tyr Ile Val Val Gly Gly Gly Ser Ala
1               5                   10

( 2 ) INFORMATION FOR SEQ ID NO: 7:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 7:

Asn Val Val Ser Lys Thr Val Xaa Leu
1               5

( 2 ) INFORMATION FOR SEQ ID NO: 8:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 8:

Met Thr Thr Gly Pro His Thr Trp Asp Leu Leu Thr Glu Pro Gln Lys
 1               5                  10                  15

(2) INFORMATION FOR SEQ ID NO: 9:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 9:

Leu Met Met Leu Ser Gly Val Gly Pro Ala
 1               5                  10

(2) INFORMATION FOR SEQ ID NO: 10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 10:

ACCWSCGGCT TYGAYTAYAT HGT 23

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 11:

TCCCANGTRT GNGGNCG 17

(2) INFORMATION FOR SEQ ID NO: 12:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 12:

CTGTGTTCTC GC 12

(2) INFORMATION FOR SEQ ID NO: 13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 13:

TCGGTTTCGC GAAGA 15

( 2 ) INFORMATION FOR SEQ ID NO: 14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 14:

CGTCTTCAAC GGAACG      16

( 2 ) INFORMATION FOR SEQ ID NO: 15:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 15:

GGAGTGACGT CCGTTC      16

( 2 ) INFORMATION FOR SEQ ID NO: 16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 16:

GAGATGTTCT CCCAGC      16

( 2 ) INFORMATION FOR SEQ ID NO: 17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 17:

TGATGGAGAA TGGCG      15

( 2 ) INFORMATION FOR SEQ ID NO: 18:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 18:

GTAATCAGAC CGACG      15

( 2 ) INFORMATION FOR SEQ ID NO: 19:

( i ) SEQUENCE CHARACTERISTICS:
        ( A ) LENGTH: 15 base pairs
        ( B ) TYPE: nucleic acid ( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 19:

TTCATTCTCG CATCC 15

( 2 ) INFORMATION FOR SEQ ID NO: 20:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 20:

GATCTCACCT TTCGC 15

( 2 ) INFORMATION FOR SEQ ID NO: 21:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 21:

CACGGATGTG AAGCC 15

( 2 ) INFORMATION FOR SEQ ID NO: 22:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 22:

GATCCTGTGT GAGCG 15

( 2 ) INFORMATION FOR SEQ ID NO: 23:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 23:

GCGATGTCAT CACGG 15

( 2 ) INFORMATION FOR SEQ ID NO: 24:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 24:

CGGTGCGTTA CGCGTCAGGA AG                                                 22

( 2 ) INFORMATION FOR SEQ ID NO: 25:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 25:

TCATGAGAAA TATTCCTACT GACCATGGTG CTGCC                                   35

( 2 ) INFORMATION FOR SEQ ID NO: 26:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: other nucleic acid (synthetic DNA)

( x i ) SEQUENCE DESCRIPTION: SEQ ID NO: 26:

CCGGAATTCC GG                                                            12

( 2 ) INFORMATION FOR SEQ ID NO: 27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 27:

AATTCGCAAT TTTTTAGTTG CATGAACTCG                                         30

( 2 ) INFORMATION FOR SEQ ID NO: 28:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 28:

AGACATGCGA GTTCATGCAA CTAAAAAATT GCG                                     33

( 2 ) INFORMATION FOR SEQ ID NO: 29:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 29:

CATGTCTCCA TAGAATGCGC GCTACTTGC                                          29

( 2 ) INFORMATION FOR SEQ ID NO: 30:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 30:

CATGGCAAGT AGCGCGCATT CTATGG      26

( 2 ) INFORMATION FOR SEQ ID NO: 31:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 31:

AATTCTGAAA TGAGCTGTTG ACAATTAATC      30

( 2 ) INFORMATION FOR SEQ ID NO: 32:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 32:

GTTCGATGAT TAATTGTCAA CAGCTCATTT CAG      33

( 2 ) INFORMATION FOR SEQ ID NO: 33:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 33:

ATCGAACTAG TTAACTAGTA CGCAAGTTC      29

( 2 ) INFORMATION FOR SEQ ID NO: 34:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 34:

CATGGAACTT GCGTACTAGT TAACTA      26

( 2 ) INFORMATION FOR SEQ ID NO: 35:

( i ) SEQUENCE CHARACTERISTICS:
        ( A ) LENGTH: 30 base pairs
        ( B ) TYPE: nucleic acid ( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 35:

AATTCTCTCT GGCGGTGTTG ACATAAATAC 30

( 2 ) INFORMATION FOR SEQ ID NO: 36:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 36:

GCCAGTGGTA TTTATGTCAA CACCGCCAGA GAG 33

( 2 ) INFORMATION FOR SEQ ID NO: 37:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 37:

CACTGGCGGT GATACTGAGC ACATCAGCC 29

( 2 ) INFORMATION FOR SEQ ID NO: 38:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 38:

CATGGGCTGA TGTGCTCAGT ATCACC 26

( 2 ) INFORMATION FOR SEQ ID NO: 39:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 39:

AATTCGGCAC CCCAGGCTTT ACACTTTATG 30

( 2 ) INFORMATION FOR SEQ ID NO: 40:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO: 40:

AGCCGGAAGC ATAAAGTGTA AAGCCTGGGG TGCCG 35

( 2 ) INFORMATION FOR SEQ ID NO: 41:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid (synthetic DNA)

( x i ) SEQUENCE DESCRIPTION: SEQ ID NO: 41:

CTTCCGGCTC GTATAATGTG TGGAATTGTC 30

( 2 ) INFORMATION FOR SEQ ID NO: 42:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: other nucleic acid (synthetic DNA)

( x i ) SEQUENCE DESCRIPTION: SEQ ID NO: 42:

CATGGACAAT TCCACACATT ATACG 25

( 2 ) INFORMATION FOR SEQ ID NO: 43:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid (synthetic DNA)

( x i ) SEQUENCE DESCRIPTION: SEQ ID NO: 43:

AATTCATCAA AAAAATATTC TCAACATAAA 30

( 2 ) INFORMATION FOR SEQ ID NO: 44:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: other nucleic acid (synthetic DNA)

( x i ) SEQUENCE DESCRIPTION: SEQ ID NO: 44:

AAAGTTTTTT ATGTTGAGAA TATTTTTTTG ATG 33

( 2 ) INFORMATION FOR SEQ ID NO: 45:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: other nucleic acid (synthetic DNA)

( x i ) SEQUENCE DESCRIPTION: SEQ ID NO: 45:

AAACTTTGTG TAATACTTGT AACGCTACC 29

-continued ( 2 ) INFORMATION FOR SEQ ID NO: 46:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 46:

CATGGGTAGC GTTACAAGTA TTACAC        26

( 2 ) INFORMATION FOR SEQ ID NO: 47:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 47:

AGCCGATGAT TAATTGTCAA CAGCTCATTT CAG        33

( 2 ) INFORMATION FOR SEQ ID NO: 48:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 48:

ATCGGCTCGT ATAATGTGTG GAATTGTC        28

METHOD FOR PRODUCING 2-KETO-L-GULONIC ACID

TECHNICAL FIELD

The present invention relates to a method for producing 2-keto-L-gulonic acid (hereinafter also referred to as 2KLGA), which is a precursor of L-ascorbic acid, efficiently and with ease by genetic engineering.

The present invention also relates to a series of expression systems involved in the efficient production of 2KLGA.

BACKGROUND ART

The 2KLGA is a key intermediate in the synthesis of L-ascorbic acid. For industrial production, 2KLGA is chemically synthesized from D-sorbitol by oxidation according to the Reichstein's method. Meanwhile, many microorganisms inclusive of the microorganisms belonging to the genus Gluconobacter are known to convert D-sorbitol to 2KLGA through an enzymatic oxidation. The microorganisms belonging to the genus Gluconobacter have been improved by genetic engineering using conjugal transfer and transposon. However, because of the low production of 2KLGA by these microorganisms, they have not been utilized in the industrial production yet.

Accordingly, there has been a desire for a more efficient and simplified method for the production of 2KLGA.

It is also well known that, in secondary metabolite production by microorganisms such as that of 2KLGA, a mere insertion of a gene (group) responsible for the biosynthesis of a substance into a plasmid and culture of the cells of microorganism, which have been recombined with this plasmid, does not necessarily result in an improved production of the desired substance, but rather, may degrade the productivity [Thomas, D. I. et al., J. Gen. Microbiol., 137, pp. 2331–2337 (1991)].

DISCLOSURE OF THE INVENTION

An object of the present invention is to provide an expression vector containing both a DNA encoding L-sorbose dehydrogenase (hereinafter SDH) and a DNA encoding L-sorbosone dehydrogenase (hereinafter SNDH), a transformant having an ability to produce 2KLGA at high yields from D-sorbitol, which has been transformed with said expression vector, and an efficient and simplified process for producing 2KLGA, which comprises culturing said transformant.

In an attempt to accomplish the above-mentioned objects, the present inventors have conducted intensive studies to succeed in obtaining an expression vector having the above-mentioned preferable property, and found that 2KLGA can be efficiently produced from D-sorbitol by a series of culture systems which comprise introducing said expression vector into a host microorganism capable of producing L-sorbose at high yields and having low 2KLGA-decomposing activity, or a host microorganism having, in addition to the above-mentioned properties, low L-idonic acid-producing activity, which resulted in the completion of the present invention.

Accordingly, the present invention relates to an expression vector containing both a DNA encoding SDH (hereinafter also referred to as SDH gene) and a DNA encoding SNDH (hereinafter also referred to as SNDH gene).

The present invention also relates to a microorganism capable of producing L-sorbose at high yields from D-sorbitol and having no or low 2KLGA-decomposing activity, or a host microorganism having, in addition to the above-mentioned properties, no or low L-idonic acid-producing activity. This microorganism is useful as a host into which the above-mentioned expression vector is introduced. The expression vector of the present invention includes not only that having an SDH gene and an SNDH gene on one vector, but also a pair of vectors separately having each gene.

The present invention further relates to a transformant which is a microorganism having the above-mentioned expression vector introduced therein, and which has an ability to produce 2KLGA at high yields from D-sorbitol.

In addition, the present invention relates to a process for producing 2KLGA, which comprises harvesting 2KLGA from a culture obtained by culturing said transformant in a medium containing D-sorbitol.

The present invention moreover relates to an expression vector, a host, a plasmid and a transformation method useful for efficiently and easily producing 2KLGA from D-sorbitol by genetic recombination.

Figure 1:
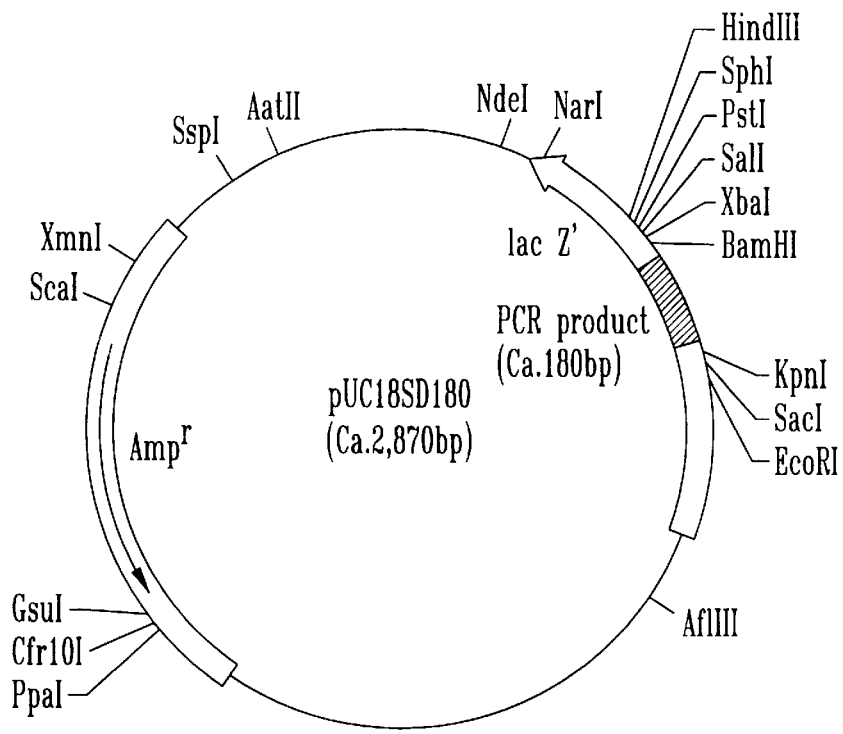
FIG. 1 is a restriction enzyme map of plasmid pUC18SD180.

DETAILED DESCRIPTION OF THE INVENTION (1) Expression vector

The expression vector of the present invention contains both a DNA encoding SDH and a DNA encoding SNDH.

The expression vector of the present invention is a DNA molecule incorporating an SDH gene and an SNDH gene in an expressionable state, which encompasses any vehicle capable of autoreplication in a host microorganism or capable of being integrated into a genome of host microorganism.

Preferred are expression vectors suitable for transforming a host microorganism capable of producing L-sorbose at high yields from D-sorbitol and having no or low 2KLGA-decomposing activity, or a host microorganism having, in addition to the above-mentioned properties, no or low L-idonic acid-producing activity, into a microorganism capable of producing 2KLGA from D-sorbitol at high yields.

Such expression vector is exemplified by vectors preferably containing, at least, a promoter having a high promoter activity in a microorganism capable of producing L-sorbose at high yields from D-sorbitol, an SDH gene, an SNDH gene, an autoreplicatable unit, and optionally a terminator region, which can be stably present in said microorganism. More preferred are those suitable for transforming a host microorganism belonging to the genus Gluconobacter or Acetobacter which is capable of producing L-sorbose at high yields from D-sorbitol, and which has no or low 2KLGA-decomposing activity, or a host microorganism having, in addition to the above-mentioned properties, no or low L-idonic acid producing activity, into a microorganism capable of producing 2KLGA from D-sorbitol at high yields.

The use, as such expression vector, of a shuttle vector containing, in addition to an autoreplicatable unit which functions stably in a host microorganism, an autoreplicatable unit of a microorganism, such as *Escherichia coli*, suitable for cloning of said expression vector, is particularly advantageous. A shuttle vector containing a marker gene, such as an antibiotic resistant gene, is more advantageous.

Examples of preferable shuttle vector in the present invention include pFG14A and pFG14B which are combined plasmids of pHSG298 and pF3, and pFG15A and pFG15B which are combined plasmids of pHSG298 and pF4.

The marker gene to be used here is exemplified by drug resistant genes such as kanamycin resistant gene, ampicillin resistant gene, chloramphenicol resistant gene and hygromycin resistant gene, auxotrophic gene and enzyme gene such as lacZ.

The promoter to be used for the expression vector of the present invention is not particularly limited as long as it has a promoter activity to transcribe SNDH and/or SDH gene in a host microorganism. A promoter having a high promoter activity to transcribe SNDH and/or SDH gene in a host microorganism capable of producing L-sorbose at high yields from D-sorbitol, is particularly preferable. As such promoter, a promoter region of SNDH gene and a part thereof having a promoter activity are exemplified. Specific examples thereof include a promoter region of SNDH gene derived from *Gluconobacter oxydans* T-100, which is included in the Sequence Listing, SQ ID:No. 5, nucleotides 1–1040, and a part thereof having a promoter activity. Examples of the promoter include promoters derived from *Escherichia coli*, such as tufB, λPL, trp, tac, lacUV5, lap, lac, ompA, phoA, recA and rrnb promoters, with preference given to tufB, λPL, trp and tac promoters. The sequences other than −35 region and −10 region may be appropriately selected to be suitable for the construction of plasmid.

The autoreplicatable unit is a DNA compound capable of replicating the DNA sequence belonging thereto in a host cell, and may include autoreplicatable unit derived from natural plasmid, artificially modified plasmid (e.g. DNA fragment prepared from natural plasmid) and synthetic plasmid.

The autoreplicatable unit in the present invention can be appropriately selected according to the microorganism to be used as a host. Preferred is an autoreplicatable unit derived from a plasmid obtained from a microorganism of the same kind with the host. For example, when the host is a microorganism belonging to the genus Gluconobacter, a plasmid derived from the genus Gluconobacter is preferably used.

The plasmid containing such autoreplicatable unit is 1–100 kb, preferably 1–10 kb in size, and advantageously has a useful restriction enzyme recognition site.

The useful restriction recognition enzyme site here means that wherein a cleavage site of a certain restriction enzyme is limited, which does not lose the activity of replicatable unit when cleaved by said restriction enzyme or when a DNA sequence is inserted in this site. Accordingly, it is advantageous in that cleavage and insertion of optional DNA at said site can be manipulated freely. Examples of such plasmid include plasmid pF3 derived from Gluconobacter IAM12138 and plasmid pF4 derived from Gluconobacter T-100.

The autoreplicatable unit of a microorganism which is suitable for cloning is not subject to any particular limitation as long as it is a replicatable unit of a plasmid derived from a microorganism generally used for cloning in the field of genetic engineering. Preferable examples include replicatable units derived from plasmids pBR322, pUC18, pHSG298, pHSG396, pACYC184 and pACYC177, and artificially modified plasmids thereof (e.g., DNA fragment obtained from a suitable restriction enzyme treatment of pBR322) derived from *E. coli*, and replicatable units derived from yeast 2μ plasmid derived from yeast.

The mode of presence of SDH gene and SNDH gene in the expression vector of the present invention is not particularly limited as long as it allows expression of SDH and SNDH.

For example, the expression vector of the present invention may contain said gene in a mode wherein the transcription and translation of SDH gene and SNDH gene are controlled by different expression systems, or wherein the both genes are controlled by a set of expression systems.

The expression vector of the former mode is exemplified by an expression vector wherein respective genes are constructed such that a transcription of each gene occurs under the control of a different promoter, and the expression vector of the latter mode is exemplified by an expression vector wherein SDH gene and SNDH gene are constructed such that transcriptions occur successively from one promoter.

The expression vector of the present invention may contain plural SDH genes and/or SNDH genes.

The DNA encoding SDH and the DNA encoding SNDH to be used in the present invention may be any as long as they encode enzymes having an SDH activity and enzymes having an SNDH activity, and are exemplified by cytoplasmic or membrane-bound SDH and SNDH, and co-enzyme dependent or independent SDH and SNDH. Preferred are a gene encoding an enzyme derived from a microorganism and a gene encoding a mutant thereof. Examples of the microorganism include those belonging to the genus Gluconobacter or Acetobacter, specifically *Gluconobacter oxydans* T-100 (FERM BP-4188).

The membrane-bound SDH derived from *Gluconobacter oxydans* T-100 is exemplified by an enzyme characterized by the following (1)–(3):

(1) an ability to catalyze the conversion of L-sorbose into L-sorbosone, (2) a molecular weight of 58,000 daltons (SDS-PAGE), and (3) an N-terminal amino acid sequence of Thr-Ser-Gly-Phe-Asp-Tyr-Ile-Val-Val-Gly-Gly-Gly-Ser-Ala-(SEQ ID NO:6).

Said SDH gene is more preferably a DNA encoding a protein having an amino acid sequence depicted in Sequence Listing, SQ:ID No. 1 to be mentioned later, and most preferably a DNA having a nucleotide sequence depicted in Sequence Listing, SQ:ID No. 3.

The cytoplasmic SNDH derived from *Gluconobacter oxydans* T-100 is exemplified by an enzyme characterized by the following (1)–(3):

(1) an ability to catalyze the conversion of L-sorbosone into 2-keto-L-gulonic acid, (2) a molecular weight of 50,000 daltons (SDS-PAGE), and (3) an N-terminal amino acid sequence of Asn-Val-Val-Ser-Lys-Thr-Val-Xaa-Leu (SEQ ID NO:7 Xaa being an unidentified amino acid).

Said SNDH gene is more preferably a DNA encoding a protein having an amino acid sequence depicted in Sequence Listing, SQ:ID No. 2 to be mentioned later, and most preferably a DNA having a nucleotide sequence depicted in Sequence Listing, SQ:ID No. 4.

Examples of suitable expression vector in the present invention are pSDH145 and pSDH155 (FERM BP-4522).

The expression vector of the present invention can be also prepared by a conventional method (e.g. digestion with restriction enzyme, ligation using T4 DNA ligase) using, if necessary, a suitable DNA fragment, by linking the above-mentioned expression system, DNA encoding SDH and DNA encoding SNDH, which are circularly linked with an adequate autoreplicatable unit.

(2) Host microorganism

The microorganism to be used as a host in the present invention is a microorganism capable of producing L-sorbose at high yields from D-sorbitol, and has no or low 2KLGA-decomposing activity. Preferably, it has, in addition to the above-mentioned properties, no or low L-idonic acid-producing activity.

That is, it is important in the present invention that the host has high conversion efficiency of D-sorbitol into L-sorbose; has low L-sorbose-metabolizing activity or even if it metabolizes, the activity to metabolize L-sorbose into a substance outside the metabolic pathway from L-sorbose into 2KLGA is very weak; and has low 2KLGA-decomposing activity.

Preferably, such microorganism can grow at a high D-sorbitol concentration of preferably not less than 5%, more preferably not less than 15%, and can convert D-sorbitol into L-sorbose at a nearly 100% efficiency. Examples of such microorganism include microorganisms belonging to the genus Gluconobacter or Acetobacter, such as *Gluconobacter oxydans* G624 (FERM BP-4415) and *Gluconobacter oxydans* NB6939.

(3) Transformant

The transformant of the present invention can be prepared by introducing the above-mentioned expression vector into a host cell. The transformant of the present invention can be also prepared by introducing SDH gene and SNDH gene into different expression vectors, and incorporating them into the cell of a host microorganism.

The method for preparing the transformant is not particularly limited, and can be appropriately determined according to the host microorganism. For example, when a microorganism belonging to the genus Gluconobacter or Acetobacter is used as a host, electroporation [Dower, W. J., Miller, J. F. and Ragsdale, C. W., Nucleic Acid Res. Vol. 16, p. 6127 (1988)] is advantageously used, since the methods generally used for transformation show low transformation efficiency. This electroporation may be carried out by a method routinely used in the field of genetic engineering, or upon modification as appropriate according to the host microorganism to be transformed.

The present invention also relates to a method for producing a competent cell suitable for the above-mentioned electroporation.

The competent cell suitable for the above-mentioned electroporation is preferably prepared by culture of a host microorganism belonging to the genus Gluconobacter or Acetobacter, which is capable of producing L-sorbose at high yields from D-sorbitol, and has no or low 2KLGA-decomposing activity, or a host microorganism which has, in addition to the above-mentioned properties, no or low L-idonic acid-producing activity, in a medium containing D-mannitol.

The transformant thus produced has an ability to produce 2KLGA at high yields from D-sorbitol as a starting material.

In the present invention, whether or not the host has been correctly transformed can be examined by determining a selection marker that the transformant has, such as a gene having resistance to antibiotics such as resistance to kanamycin, and enzyme genes, such as auxotrophic gene and LacZ gene, or by determining SDH activity and SNDH activity that the transformant has.

(4) Process for producing 2KLGA

The 2KLGA of the present invention is obtained by culturing the above-mentioned transformant having an expression vector in a medium containing D-sorbitol, and harvesting 2KLGA from the obtained culture.

While the preferable composition of the nutrient medium to be used varies depending on the host, it generally contains D-sorbitol and may contain carbon sources such as D-mannitol, D-glucose, D-fructose, L-sorbose and glycerol. It is preferable that it further contain inorganic or organic nitrogen sources (e.g., ammonium sulfate, ammonium chloride, hydrolysate of casein, yeast extract, polypeptone, Bactotrypton, beef extract and corn steep liquor). If desired, other nutritious sources such as inorganic salts (e.g., disodium hydrogenphosphate, sodium dihydrogenphosphate, dipotassium hydrogenphosphate, potassium dihydrogenphosphate, magnesium chloride, magnesium sulfate, calcium carbonate and calcium chloride), vitamins (e.g., vitamin $B_1$), and antibiotics (e.g., ampicillin, kanamycin, tetracyclin and chloramphenicol) may be added to the medium.

When a microorganism belonging to the genus Gluconobacter is used as a host, a medium containing D-sorbitol, yeast extract and calcium carbonate may be used.

The concentration of D-sorbitol in the medium is generally 1–30%, preferably 5–20%.

The transformant is cultured under the conditions which permit production of 2KLGA at high yields, according to the host microorganism to be used. For example, when a microorganism belonging to the genus Gluconobacter is used, pH is generally 5.5–8.5, preferably 7–7.5, culture temperature is generally 18°–40° C., preferably 20°–30° C., and culture time is generally 20–170 hours.

The 2KLGA thus produced is generally contained in solution fractions in the culture. Thus, 2KLGA can be purified by obtaining a culture filtrate by filtration or centrifugation of the culture and purification of the culture filtrate by a method generally used for purification, such as column chromatography on a suitable adsorbent and crystal precipitation.

Commercially available plasmid, restriction enzyme, enzyme such as T4 DNA ligase and other substances used in the following Examples were used according to the instructions of the suppliers. Cloning of DNA, culture of transformant, recovery of 2KLGA from the obtained culture are well-known to those skilled in the art, or can be known from published literatures.

*Gluconobacter oxydans* T-100 (FERM BP-4188), *Gluconobacter oxydans* G624 (FERM BP-4415), *Glucono-*

*bacter oxydans* GA-1 (G624-pSDH155) (FERM BP-4522) and *Gluconobacter oxydans* N952 (NB6939-pSDH155) (FERM BP-4580) have been internationally deposited at National Institute of Bioscience and Human-Technology, Agency of Industrial Science and Technology, Japan.

According to the present invention, 2KLGA useful for the production of L-ascorbic acid can be produced with ease and in larger amounts by a single operation of culture.

The present invention is explained in more detail in the following by way of Examples, to which the present invention is not limited.

EXAMPLE 1

Purification of SDH from *Gluconobacter oxydans* T-100

(1) Microorganism

*Gluconobacter oxydans* T-100 was selected as a 2KLGA-high-producing mutant derived from *Gluconobacter oxydans* G716 (wild strain) by nitrosoguanidine (NTG) mutagenesis.

(2) Cultivation of *Gluconobacter oxydans* T-100

Single colonies of *Gluconobacter oxydans* T-100 were transferred into 6 independent culture media (100 ml each) consisting of 2.5% glucose, 1.0% polypeptone, 0.5% yeast extract (Difco Labs., USA) and 2.0% $CaCO_3$ in 500 ml Erlenmeyer flasks. The cultivation was performed at 30°0 C. on a rotary shaker (250 rpm) for 18 hours. The cultivated medium (total 600 ml) was inoculated to 20 liters of a fermentation medium containing 5% D-sorbitol, 0.5% glycerol, 0.5% yeast extract and 1.0% $CaCO_3$ in a 30 L jar. Cultivation was carried out at 30° C. for 42 hours under aeration at 20 liters/min and agitation at 300 rpm. The cultivated broth (20 L) was centrifuged at 6,000 rpm at 4° C. for 10 min. The cells were washed once with cold saline and recentrifuged under the same conditions. The cells were stored at −20°0C. until use.

(3) Preparation of the membrane fraction

Cells (17.7 g, wet weight) obtained in (2) were suspended in 50 ml of 10 mM phosphate buffer (pH 7.0), disrupted by sonication, and centrifuged at 8,000 rpm at 4° C. for 10 min to give a supernatant. On the other hand, the resulting precipitates were suspended in 40 ml of 10 mM phosphate buffer (pH 7.0), sonicated for disruption and centrifuged under the same conditions as above. The supernatants were pooled and ultracentrifuged at 32,000 rpm at 4° C. for 60 min. The resulting precipitates were washed once with phosphate buffer (50 ml) and subjected to ultracentrifugation under the same conditions as above to give crude membrane proteins (membrane fraction).

(4) Solubilization of SDH from the membrane fraction

The membrane fraction obtained in (3) as suspended in 50 ml of 10 mM phosphate buffer (pH 7.0). To the suspension, 0.75 ml of 20% Triton X-100 (Nacalai Tesque, Japan) and 1.8 g of L-sorbose were added, and the mixture was stirred on ice for 3.5 hours. The resultant suspension was ultracentrifuged at 32,000 rpm at 4° C. for 60 min to give a supernatant (ca. 48 ml), designated as solubilized SDH fraction.

(5) Ion-exchange chromatography

The solubilized fraction (16 ml) obtained in (4) was subjected to ion-exchange chromatography on a TSKgel DEAE-5PW column (7.5 mm inner diameter×75 mm, Toso Co. Ltd., Japan) equilibrated with 10 mM phosphate buffer (pH 7.0) containing 0.3% Triton X-100 and 200 mM L-sorbose. The column was eluted with a linear gradient of sodium chloride from 0M to 0.5M in an equilibration buffer. Enzyme activity was assayed according to T. SUGISAWA et al. (Agric. Biol. Chem., Vol. 55, 363–370, 1991) using L-sorbose as a substrate and 0.1 mM 2,6-dichlorophenolindophenol (DCIP) as an electron acceptor in 0.28M phosphate buffer (pH 7.0). One enzyme unit was defined as the amount of the enzyme that catalyzes the reduction of 1 μmole DCIP per minute. The reduction of DCIP was determined by the decrease of absorbance at 600 nm with spectrophotometer (Model UV-160, Shimadzu, Japan). Active fractions were pooled, diluted 3-fold with 10 mM phosphate buffer (pH 7.0), and applied to a DEAE-TOYOPEARL 650M column (7.0 mm inner diameter×7 mm, Toso Co. Ltd., Japan) equilibrated with 10 mM phosphate buffer (pH 7.0). The column was eluted with 0.2M sodium chloride in an equilibration buffer. The resulting eluate was used for further purification steps.

(6) Gel-filtration chromatography

A portion (300 μl) of the concentrated active fraction was subjected to gel-filtration chromatography on a Superose 12 HR10/30 column (10 mm inner diameter×30 cm, Pharmacia, Sweden) equilibrated with 10 mM phosphate buffer (pH 7.0) containing 0.3% Triton X-100, 200 mM L-sorbose and 0.2M sodium chloride. Elution was performed using the same buffer. Each fraction (0.4 ml) was analyzed by polyacrylamide gel electrophoresis in the presence of sodium dodecyl sulfate (SDS-PAGE, 12.5% gel) and by enzyme assay described in Example 1 (5). From the analysis of SDS-PAGE, SDH activity was found to correspond to 58 kd protein, suggesting that the 58 kd protein was the desired SDH molecule.

EXAMPLE 2

Amino acid sequence analysis of SDH

The concentrated active fraction (15 μl) was subjected to SDS-PAGE (12.5% gel) and the separated proteins were blotted on a polyvinylidene difluoride (PVDF) membrane. The membrane containing 58 kd protein stained by ponceau S was cut out and washed with distilled water. The membrane piece was directly sequenced with an automated protein sequencer Model 470A (Applied Biosystems Inc., USA) for N-terminal amino acid sequence analysis.

To determine the internal amino acid sequence, fragmentation with achromobacter protease I (Wako Chemical, Japan) was carried out on the surface of the membrane. The fragments obtained were eluted with 50 mM Tris-HCl (pH 9.0) containing 8% acetonitrile, and separated by reversed phase chromatography using Cosmosil 5C4-300 (4.6 mm inner diameters ×50 mm, Nacalai Tesque, Japan) with a linear gradient elution (75 min) of acetonitrile of from 8% to 83% in 0.05% trifluoroacetic acid. Two kinds of peptides (Peptide 1 and Peptide 2) were isolated, and sequenced with an automated protein sequencer Model 470A for amino acid sequence identification. The resultant data are shown in Table 1 (SEQ ID NO:6,8,9).

TABLE 1

| | |
|---|---|
| $NH_2$-terminal sequence | TSGFDYIVVGGGSA |
| Peptide 1 | MTTGPHTWDLLTEPQK |
| Peptide 2 | LMMLSGVGPA |

EXAMPLE 3

Preparation of DNA probe (1) Synthesis of DNA oligomers

Each oligonucleotide listed in Table 2 below was synthesized by phospho amidite method using DNA synthesizer model 392 (Applied Biosystems Inc., USA) (SEQ ID NO:10,11). The synthesized oligonucleotide was liberated from CPG polymer support (CPG: controlled pore glass) with 28% aqueous ammonia, followed by heating at 60° C. for 9 hours to remove all protective groups. The reaction mixture was evaporated in vacuo, and the residue was dissolved in 200 μl of TE [10 mM Tris-HCl (pH 7.4)-1 mM EDTA]. The resulting solution was washed once with ether and precipitated with ethanol. The obtained oligonucleotides were used as primers for polymerase chain reaction without further purification.

TABLE 2

Oligonucleotide encoding NH$_2$-terminal sequence (forward primer)
5' > ACC (TA)(GC)C GGC TT(TC) GA(TC) TA(TC) AT(TCA) GT < 3'
Oligonucleotide encoding internal sequence (reverse primer)
5' > TC CCA (ATCG)GT (AG)TG (ATCG)GG (ATCG)CG < 3'

(2) Preparation of chromosomal DNA single colony of *Gluconobacter oxydans* T-100 was cultivated in a medium (100 ml) consisting of 2% glucose, 1% polypeptone and 0.5% yeast extract at 37° C. for 24 hours. The cells were collected by centrifugation (4,600 rpm, 10 min) and suspended in TE buffer (2.5 ml). A portion (2.0 ml) of the suspension was diluted with 20 ml of STE buffer [20% sucrose-50 mM Tris-HCl (pH 8)-1 mM EDTA], mixed with 5 ml of lysozyme solution (5 mg/ml), and incubated at 37° C. for 30 min. Sarcosil solution [1% lauroyl sarcosilate-100 mM EDTA (pH 9.0)] (50 ml) and proteinase K (40 mg) were added, and the mixture was incubated at 50° C. for 1.5 hours. Cesium chloride (93.8 g) and 6 ml of ethidium bromide (5 mg/ml) were dissolved in 75 ml of said mixture, and the cesium chloride solution was ultracentrifuged at 50,000 rpm at 20° C. for 14 hours. The portion containing chromosomal DNA was isolated, washed twice with isopropyl alcohol saturated with physiological saline, and dialyzed against TE buffer (2 L) for 4 hours. The dialysate was extracted with phenol (20 ml), and dialyzed twice against TE buffer (2 L) to give the desired chromosomal DNA solution (14 ml, 91.5 μg/ml).

(3) Polymerase chain reaction

Polymerase chain reaction (PCR) was carried out with 180 ng of *Gluconobacter oxydans* T-100 chromosomal DNA and 2.5 pmoles of each primer of Table 2, using Hybaid thermal reactor Model HB-TRL1 (Hybaid Limited, UK). The reaction mixture [200 μM dNTPs each and 2.5 units Taq DNA polymerase in PCR buffer (Perkin Elmer-Cetus, USA)] was subjected to 50 cycles of PCR, each consisting of 0.5 min of denaturation at 95° C., 1 min of annealing at 42° C. and 2 min of polymerization at 72° C. A single fragment was obtained by PCR. The DNA fragment (180 bp) supposedly coding for a part of the SDH gene was isolated by 1.5% agarose gel-electrophoresis and filled with DNA polymerase Klenow fragment (Takara Shuzo, Japan) to give a blunt-ended DNA. The resultant DNA and pUC18 (Nippon Gene, Japan) previously digested with SmaI were ligated in the presence of T4 DNA ligase (Takara Shuzo, Japan). The ligation mixture was used to transform *E. coli* JM109 (Nippon Gene, Japan) according to the procedure of SHIGE-SADA et al. (*Saibo-kogaku*, 2, 616–626, 1983). From one of the transformants, the desired plasmid pUC18SD180 (see FIG. 1) was obtained and characterized by restriction mapping.

(4) Preparation of the $^{32}$P-labelled probe

The insert DNA (ca. 200 bp) was isolated by digestion of pUC18SD180 with BamHI and EcoRI (Nippon Gene, Japan). The ca. 200 bp DNA was purified by 0.5% agarose gel-electrophoresis. Purified DNA was $^{32}$P-labelled with nick translation kit (Takara Shuzo, Japan) according to the appended protocols. The specific activity of DNA labelled with 32P was about $3.7 \times 10^7$ cpm/μg.

EXAMPLE 4

Isolation of SDH gene from *Gluconobacter oxydans* T-100 DNA library (1) Preparation of chromosomal DNA library The genomic DNA obtained in Example 3 (2) was partially digested with MboI (Nippon Gene, Japan) and the fragments were separated on a sucrose gradient to produce a fragment with a size range of from 8 kbp to 22 kbp before cloning into the BamHI site of lambda phage vector EMBL-3 (Clonetech). This lambda phage vector was introduced into *E. coli* NM538 (Clonetech) to construct Gluconobacter T-100 chromosomal DNA library.

(2) Plaque hybridization

Preparation of lambda phage plaques with *E. coli* NM538 (Clonetech) as a plating bacterium and immobilization of the plaques on the nitrocellulose filter were carried out according to the protocols described in Molecular Cloning vol. 1, Chapter 2, page 108, 1989, USA. The filters containing the lambda DNA were incubated in a hybridization buffer (50% formamide-1% bovine serum albumin-0.1% polyvinyl pyrrolidone-0.1% ficoll-5×SSPE (see Molecular Cloning)-0.1% SDS-100 μ/ml salmon sperm DNA) at 42° C. for 4 hours, in the same buffer but containing $^{32}$P-labelled probe (ca. 200 bp, ca. $1 \times 10^7$ cpm/ml) at 42° C. for 18 hours and in 2×SSC (see Molecular Cloning) containing 0.05% SDS at 42° C. successively to remove the excess probe. The filters were exposed to an X-ray film HR-H (Fuji Film, Japan) at −80° C. for 18 hours. As a result of the first screening of lambda phage library, about 30 positive phages were obtained from 72,000 plaques.

(3) Southern blotting

Figure 2:
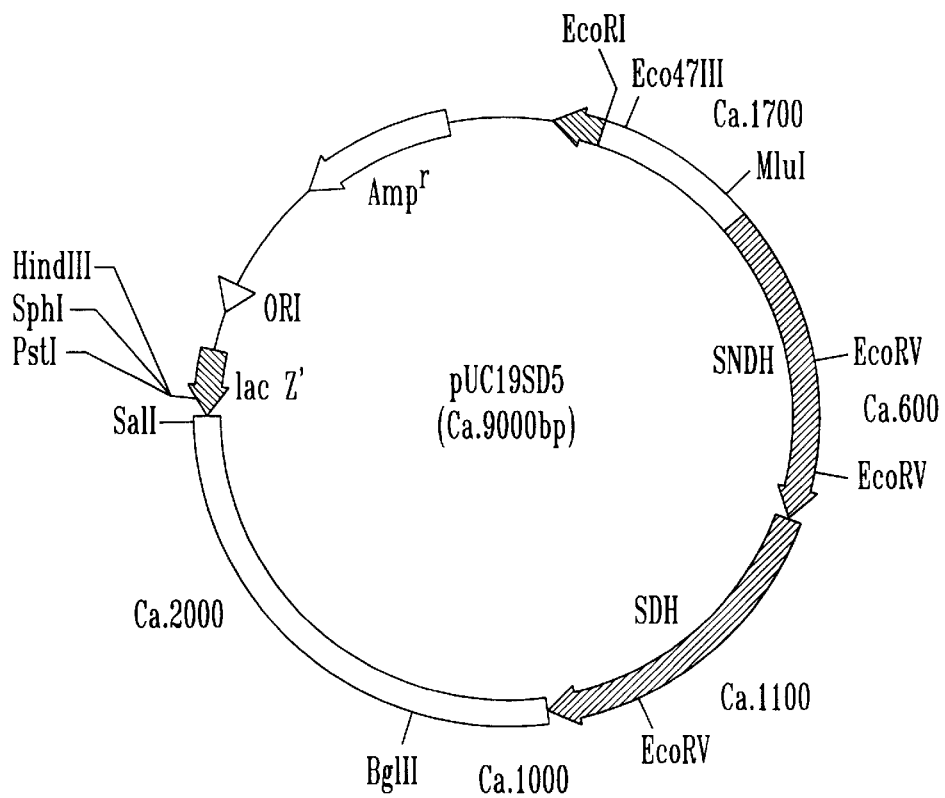
FIG. 2 is a restriction enzyme map of plasmid pUC19SD5.

One of the positive phage DNAs was digested with EcoRI and SalI (Nippon Gene, Japan) and subjected to 0.8% agarose gel electrophoresis. The DNA fragments separated on the gel were transferred onto a nitrocellulose filter by electroblotting. Approximately 6 kbp DNA fragment was identified to hybridize the $^{32}$P-labelled probe. It was cloned into between the EcoRI site and SalI site of pUC19 (Nippon Gene, Japan) to give pUC19SD5 (FIG. 2).

EXAMPLE 5

DNA sequence analysis of SDH gene (1) Construction of the plasmids for DNA sequence Construction of plasmid pSD5RRV pUC19SD5 was digested with EcoRV (Toyobo, Japan). From among the three bands separated by 1.5% agarose gel-electrophoresis, 1.1 kbp DNA which hybridizes the $^{32}$P-labelled probe was isolated and cloned into the SmaI site of pUC18 to give the plasmid pSD5RRV.

(2) Construction of plasmid pSD5RVS pUC19SD5 was digested with EcoRV and Eco47III (Toyobo, Japan). The large DNA (ca. 5,700 bp) was isolated and self-ligated with T4 DNA ligase (Takara Shuzo, Japan) to give the plasmid pSD5RVS.

(3) DNA sequence analysis

DNA sequence analysis of the template DNA (pSD5RRV and pSD5RVS) was performed by dideoxy termination method with 370A DNA sequencer (Applied Biosystems, USA) according to appended protocols. The M13 sequencing primers, universal and reverse primers (New England Biolabs, USA) were used for the first sequencing. Based on the DNA sequence determined by the first sequence analysis, the following primers were synthesized and used for further DNA sequence analyses. The synthesized primers used are shown in Table 3 (SEQ ID NO:12–16).

TABLE 3

| | |
|---|---|
| Primer 1 (12 mer): | 5' > CTG TGT TCT CGC < 3' |
| Primer 2 (15 mer): | 5' > TCG GTT TCG CGA AGA < 3' |
| Primer 3 (16 mer): | 5' > CGT CTT CAA CGG AAC G < 3' |
| Primer 4 (16 mer): | 5' > GGA GTG ACG TCC GTT C < 3' |
| Primer 5 (16 mer): | 5' > GAG ATG TTC TCC CAG C < 3' |

As a result of the analysis, an open reading frame (ORF) consisting of 1596 base pairs was found. The amino acid sequence encoded by the nucleotide sequence beginning from the initiation codon (ATG) of the ORF coincided with the amino acid sequence of SDH which was obtained in Example 2, and the theoretical molecular weight of the protein encoded by the ORF, of 58 kd coincided well with the apparent molecular weight of SDH, 58 kd by SDS-PAGE. Therefore, the ORF was determined to be the SDH gene.

The nucleotide sequence of the SDH gene is shown in the Sequence Listing, Sequence No. 3 to be mentioned later, and the amino acid sequence deduced from the nucleotide sequence is shown in Sequence No. 1.

EXAMPLE 6

Expression of SDH gene in *E. coli*

(1) Cultivation of the transformed (transfected) *E. coli*

A single colony of *E. coli* JM109 transformed with pUC19SD5 (*E. coli* JM109-pUC19SD5) was inoculated into 100 ml of a medium containing 1% Bactotrypton (Difco Labs., USA), 0.5% yeast extract, 0.5% sodium chloride and 0.1% glucose (pH 7.2) in a 500 ml flask and cultivated at 30° C. for 18 hours. A portion of the cultured broth (3 ml of each) was transferred to two media (100 ml) containing 1% Bactotrypton, 0.5% yeast extract, 0.5% sodium chloride, 1% glycerol, 0.3% $KH_2PO_4$, 0.8% $Na_2PO_4 \cdot 12H_2O$ (pH6.8), 1% L-sorbose and 100 μg/ml of ampicillin in a 500 ml Erlenmeyer flask. The resultant mixtures were cultivated at 25° C. for 3 days. The cultured broth (total 200 ml) was harvested by centrifugation at 6,000 rpm at 4° C. for 10 min. The cells were washed twice with saline, suspended in 5 ml of the same solution, and disrupted by sonication at 30 second intervals for a total sonication time of 2 min under ice-cooling. The resultant cell lysate was stored at −20° C. until use for an enzyme assay.

(2) Assay of SDH activity

SDH expressed activity was assayed by determining the amount of the reaction product, L-sorbosone, using high performance liquid chromatography (HPLC). The reaction mixture consisting of 1% L-sorbose, 1 mM phenazine methosulfate, 0.1M phosphate buffer (pH 8.0) and the sonicated cell lysate was incubated at 30° C. with shaking for 5 hours. The reaction was stopped by adjusting pH to 2 with 6N sulfuric acid. The reaction mixture was centrifuged at 6,000 rpm at 4° C. for 10 min and a portion of the supernatant was directly analyzed by HPLC with a #3011N column (4.6 mm inner diameter×300 mm, Hitachi, Japan). The mobile phase was 1M borate buffer (pH 9.5) containing 0.02M benzamidine hydrochloride and 0.25M potassium sulfate which were used for a post column labelling method, at a flow rate of 0.8 ml per minute. The post column labelling reaction was performed at 80° C. in a Tefron tube (0.5 mm inner diameter×10 m). Detection of the labelled compound was carried out by monitoring fluorescence (Ex. 315 nm, Em. 405 nm). As shown in the following Table 4, the sonicated cells containing plasmid pUC19SD5 had an ability to convert L-sorbose to L-sorbosone. However, no activity was found in the cell lysate treated at 100° C. or the cells without the plasmid. These results indicate that the recombinant plasmid pUC19SD5 contains the gene encoding L-sorbose dehydrogenase, which expressed in *E. coli* JM109.

TABLE 4

| Strain | Theatment | L-sorbosone (μg/ml) |
|---|---|---|
| JM109 (pUC19SD5) | Sonication | 2,310 |
| JM109 (pUC19SD5) | Sonication, boiling | 24 |
| JM109 | Sonication | 21 |
| Basal | — | 33 |

EXAMPLE 7

Purification of SNDH from *Gluconobacter oxydans* T-100

(1) Preparation of crude enzyme solution

The cells (ca. 10 g, wet weight) obtained in Example 1 (2) were suspended in 40 ml of 10 mM phosphate buffer (pH 7.0) under ice-cooling, disrupted by sonication, and centrifuged at 8,000 rpm at 4° C. for 10 min. The supernatant was ultracentrifuged at 32,000 rpm at 4° C. for 60 min. The resulting supernatant was used for further determinations as an SNDH crude enzyme solution.

(2) Ion-exchange chromatography

The SNDH crude enzyme solution (45 ml) was passed through QAE-TOYOPEARL 550 C column (1.6 cm inner diameter×30 cm, Toso Co. Ltd., Japan) previously equilibrated with 10 mM phosphate buffer (pH 7.0). The column was washed with the same buffer and eluted with a linear gradient of sodium chloride of from 0M to 0.4M in the same buffer. The activity of the enzyme was assayed by the method by SUGISAWA et al. (Agric. Biol. Chem., 55, 665–670, 1991), by measuring the amount of NADH produced by the reaction in the presence of 13.7 μM L-sorbosone and 0.73 μM NAD in 50 mM phosphate buffer, which was determined by the absorbance at 340 nm. The active fractions (ca. 15 ml) were pooled and diluted 5-fold with phosphate buffer for use in the purification step to follow.

(3) Blue Sepharose chromatography

The enzyme solution (ca. 75 ml) obtained in (2) was passed through Blue Sepharose column (1.0 cm inner diameter×7 cm, Pharmacia, Sweden) previously equilibrated with phosphate buffer. The column was washed with the same buffer and eluted with a linear gradient of sodium chloride of from 0M to 0.6M in the same buffer. The respective fractions were analyzed by polyacrylamide gel electrophoresis in the presence of sodium dodecyl sulfate (SDS-PAGE) and by enzyme assay of Example 7 (2). As a result, it was found that the protein having a molecular weight of 50 kd by SDS-PAGE corresponded to the enzyme activity, suggesting that said 50 kd protein was the desired SNDH molecule.

EXAMPLE 8

SNDH amino acid sequence analysis

The active fraction (75 μl) obtained in Example 7 (3) was subjected to SDS-PAGE and the separated protein was blotted on a polyvinylidene difluoride (PVDF) membrane.

The membrane containing 50 kd protein stained by Coomassie Brilliant Blue was cut out and washed with distilled water. The membrane piece was sequenced with an automated protein sequencer Model 470A (Applied Biosystems Inc., USA) for N-terminal amino acid sequence analysis. The results are shown below wherein Xaa is an unidentified amino acid. N-terminal amino acid sequence (SEQ ID NO:7):

Asn-Val-Val-Ser-Lys-Thr-Val-Xaa-Leu-

EXAMPLE 9

DNA sequence analysis of SDNH gene (1) Construction of plasmid for nucleotide sequence analysis The plasmid pUC19SD5 (FIG. 2) obtained in Example 4 (3) was digested with SalI (Nippon Gene, Japan) and EcoRV (Toyobo, Japan) and subjected to 0.8% agarose gel electrophoresis. Of the separated DNA fragments, the fragments of about 600 bp and 4,300 bp were separated from the gel. The former was inserted into SmaI site of pUC18 to construct pSD6RRV. The latter was filled with DNA polymerase Klenow fragment (Takara Shuzo, Japan) to give a blunt-ended SalI cleavage site, followed by self-ligation to construct circular plasmid pSD5RIRV. This plasmid pSD5RIRV was digested with EcoRI and MluI, and about 3,400 bp fragment was isolated. Blunting and circularizing in the same manner as above gave pSD5MRV.

(2) Nucleotide sequence analysis

Nucleotide sequence analyses of the template DNA (pSD5MRV, pSD6RRV and pSD5RRV used for SDH nucleotide sequence analysis) were performed by dideoxy termination method with 370A DNA sequencer (Applied Biosystems, USA). The M13 sequencing primers, universal and reverse primers (New England Biolabs, USA) were used for the first sequencing. Based on the DNA sequences determined by the first sequencing, the following primers were synthesized and used for further DNA sequence analyses. The synthesized primers used were as follows (SEQ ID NO:17–23).

Primer 1 (15 mer); 5'>TGATGGAGAATGGCG<3'
Primer 2 (15 mer); 5'>GTAATCAGACCGACG<3'
Primer 3 (15 mer); 5'>TTCATTCTCGCATCC<3'
Primer 4 (15 mer); 5'>GATCTCACCTTTCGC<3'
Primer 5 (15 mer); 5'>CACGGATGTGAAGCC<3'
Primer 6 (15 mer); 5'>GATCCTGTGTGAGCG<3'
Primer 7 (15 mer); 5'>GCGATGTCATCACGG<3'

As the result of the above analyses, an open reading frame (ORF) consisting of 1497 bp was found in the upstream of 5'-side of SDH gene. The amino acid sequence encoded by the nucleotide sequence beginning from the initiation codon (ATG) of the ORF coincided with the N-terminal amino acid sequence of SNDH which was obtained in Example 8, and the theoretical molecular weight of the protein encoded by the ORF, of 53 kd coincided well with the molecular weight of SNDH, 50 kd by SDS-PAGE. Therefore, the ORF was considered to be the SNDH gene. The nucleotide sequence of the SNDH gene is shown in the Sequence Listing, Sequence No. 4 to be mentioned later, and the amino acid sequence deduced from the nucleotide sequence is shown in Sequence No. 2.

EXAMPLE 10

Expression of SNDH gene in E. coli (1) Cultivation of the transformed E. coli

In the same manner as in Example 6, cell lysate of E. coli JM109-pUC19SD5 was obtained and stored at −20° C. until use for an enzyme assay.

(2) Assay of SNDH activity

SNDH expressed activity was assayed by determining the amount of the reaction product, 2KLGA, using HPLC. The reaction mixture consisting of 1% L-sorbosone, 0.5 mM NAD, 0.1M phosphate buffer (pH 8.0) and the sonicated cell lysate was incubated at 30° C. with shaking for 5 hours. The reaction was stopped by adjusting pH to 2 with 6N sulfuric acid. The reaction mixture was centrifuged at 6,000 rpm at 4° C. for 10 min, and a portion of the supernatant was analyzed by HPLC (column Capcellpak $NH_2$; 4.6 mm inner diameter×250 mm, Shiseido, Japan). The mobile phase was 20 mM sodium phosphate buffer (pH 3.0) containing 30% acetonitrile at a flow rate of 1.2 ml per minute. Detection was carried out by measuring ultraviolet absorption at 210 nm.

As a result, the mixture containing the sonicated cell lysate of E. coli JM109-pUC19SD5 transformed with the plasmid pUC19SD5 produced 5690 µg/ml of 2KLGA, demonstrating the ability to convert L-sorbosone to 2KLGA. While the host of the transformant, E. coli JM109 itself had an ability to convert same into 2KLGA, its ability was about one-second (2170 µg/ml) of the ability possessed by the transformant, thus suggesting evident enhancement of the ability of the transformant to convert same into 2KLGA, that is, SNDH activity. Therefrom it was made clear that the recombinant plasmid pUC19SD5 had a gene encoding SNDH, and the ORF consisting of 1497 bp at the upstream of 5'-side of the SDH gene found in Example 9 was an SNDH gene.

EXAMPLE 11

Selection of host (1) Selection of cell producing sorbose at high yields

A production cell which converts D-sorbitol to L-sorbose at high yields was separated from a fruit. A small amount of separation source was added to an enrichment culture medium having a composition of potato dextrose (2.4%), ethanol (0.5%), peptone (0.3%), yeast extract (0.5%) and acetic acid (0.03%), and the medium was subjected to stationary culture at 30° C. for 5 days. A plate medium containing D-sorbitol (5%), yeast extract (0.5%), calcium carbonate (0.25%) and agar (1.5%) was used for pure isolation of the cells, and the colonies formed after culture at 30° C. for 5 days were picked up. The cells grown in the plate medium were inoculated into a test tube containing a seed medium (6 ml) containing glucose (2.5%), yeast extract (0.5%), polypeptone (1.0%) and calcium carbonate (0.5%), and cultured in a test tube shaker at 30° C. for 18 hours. A portion of the culture (0.5 ml) was inoculated into a 100 ml Erlenmeyer flask containing 15 ml of a production medium containing D-sorbitol (5%), yeast extract (0.5%) and calcium carbonate (2%), and cultured in a rotary shaker (250 rpm) at 30° C. for 4 days. The obtained L-sorbose was determined by HPLC (column OA KC 7.8 mm inner diameter×300 mm, Merck, mobile phase 0.05N sulfuric acid, flow rate 0.4 ml/min, detection by differential refractometer), whereby the cell lines having a high L-sorbose productivity were selected. The selected cell lines were screened in the above medium only different in D-sorbitol concentration which was varied to 10%, 15% and 20%, and five cell lines capable of producing L-sorbose at high yields even at high D-sorbitol concentration were selected. Of these five cell lines, G624 (FERM BP-4415) had the highest sugar resistance and converted D-sorbitol to L-sorbose at high yields (Table 5).

TABLE 5

| Cell line | D-sorbitol in medium | Amount of produced L-sorbose (g/l) | | |
|---|---|---|---|---|
| | | 100 g/l (10%) | 150 g/l (15%) | 200 g/l (20%) |
| G575 | | 96 | 149 | 4 |
| G613 | | 98 | 145 | 2 |
| G617 | | 98 | 147 | 2 |
| G624 | | 97 | 154 | 200 |
| G625 | | 102 | 98 | 4 |

(2) Selection of 2KLGA-low decomposing cells

The 2KLGA decomposability of L-sorbose high production cell G624 was examined using an ultrasonically destroyed cell system. G624 was inoculated into a test tube containing a medium (6 ml) containing glucose (2.5%), polypeptone (1.0%), yeast extract (0.5%) and calcium carbonate (0.5%), and cultured in a test tube shaker at 30° C. for 18 hours to give a seed culture. The seed culture (3 ml) was inoculated into a 500 ml Erlenmeyer flask containing 100 ml of a medium containing D-sorbitol (5%), yeast extract (0.5%) and calcium carbonate (2.0%), and cultured in a rotary shaker (250 rpm) at 30° C. for 48 hours. The obtained culture was centrifuged at 4° C., 500 rpm for 10 min to remove calcium carbonate. The supernatant was centrifuged at 4° C. rpm for 10 min to collect the cells. After two repeats of washing with physiological saline and centrifugal separation under the same conditions, the cells were again suspended in physiological saline to adjust the volume to 2.5 ml.

The cells were subjected to ultrasonication under ice-cooling at 30 seconds intervals for a total treatment time of 6 min to prepare ultrasonic rupture cells. To the ultrasonic rupture cells was added a test solution (1.0 ml) containing 2% 2KLGA, 2 mM NADPH and 0.2M phosphate buffer (pH 7.0), and the mixture was shaken in the test tube at 30° C. for 3 hours and 5 hours. The pH was adjusted to 2 with 6N sulfuric acid to terminate the reaction. The reaction mixture was centrifuged at 4° C., 6000 rpm for 10 min. The supernatant underwent determination of 2KLGA and L-idonic acid by HPLC described in Example 10 (2). The results obtained when the reaction time was 0 and when NADPH was not added shown in Table 6. It was clarified that G624 did not have 2KLGA-decomposing ability.

TABLE 6

Decomposition of 2KLGA by G624 (1% 2KLGA)

| Addition of NADPH (mM) | Reaction time (hours) | 2KLGA (mg/ml) | L-idonic acid (mg/ml) |
|---|---|---|---|
| 0 | 0 | 9.30 | 0.00 |
| | 3 | 9.00 | 0.00 |
| | 5 | 9.21 | 0.00 |
| 1 | 0 | 9.00 | 0.00 |
| | 3 | 9.23 | 0.00 |
| | 5 | 9.37 | 0.00 |

(3) Identification of cell line G624 which shows high production of sorbose and low decomposition of 2KLGA The myologial properties of G624 were analysed according to Bergey's Manual of Systematic Bacteriology [The Williams & Wilkins Company (1989)]. As a result, G624 was found to be Gram negative rod cells with G+C=57.4%, oxidase negative, catalase positive, aerobic, and utilizes ethanol, belongs to Family Acetobacteriaceae and contains ubiquinone 10 alone as cellular isoprenoidquinone. Consequently, G624 was identified to be belonging to the genus Gluconobacter. G624 was identified to be *Gluconobacter oxydans* based on DNA homology determined by DNA-DNA hybridization in a microplate using *Gluconobacter oxydans* IFO3287 and IFO3293 as type cultures.

(4) Selection of selection marker

The sensitivity to various antibiotics of G624 selected as a host was examined by agar dilution method, and the possible use of a drug resistant gene as a selection marker to be used for transformation was considered. The results are shown in Table 7.

TABLE 7

| MIC by agar dilution method (mg/ml) | |
|---|---|
| Antibiotics | MIC (μg/ml) |
| chloramphenicol | 500 |
| gentamycin | 10–50 |
| hygromycin | 50–100 |
| kanamycin | 10 |
| tetracycline | 10–50 |
| ampicillin | 500 |
| SY medium: D-sorbitol | 5.0% |
| Yeast extract | 0.5% |
| CaCO$_3$ | 0.25% |
| agar | 1.0% |

From the above results, G624 was found to be sensitive to kanamycin, and determined to be a host cell capable of utilizing kanamycin resistance as a selection marker.

EXAMPLE 12

Construction of shuttle vector

*Escherichia coli* was selected as a microorganism suitable for mass production of shuttle vector and cloning of expression vector, and a shuttle vector capable of autoreplication in both *Gluconobacter oxydans* and *Escherichia coli* was constructed.

(1) Obtaining plasmid of Gluconobacter

It was tried to obtain a plasmid from a type culture and natural culture isolate of Gluconobacter to obtain an autoreplicatable unit of Gluconobacter.

Figure 3:
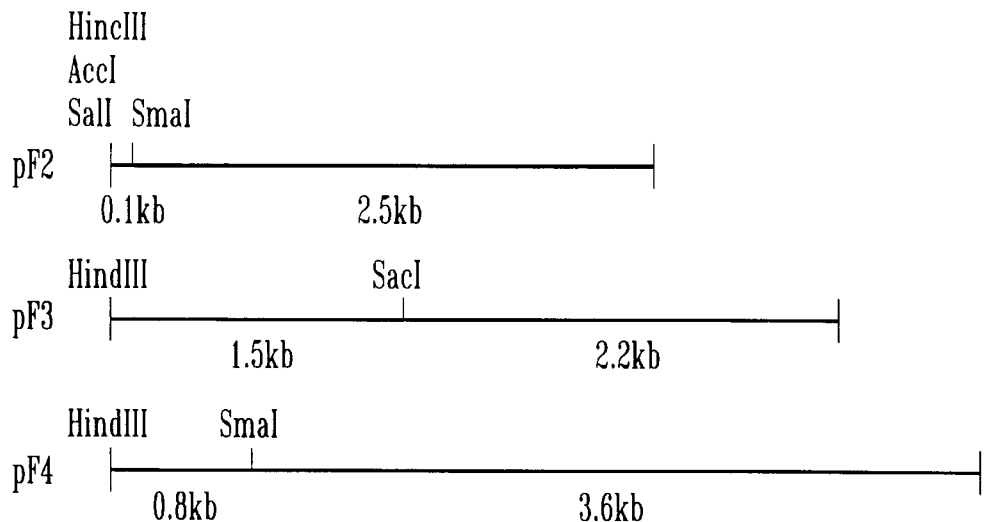
FIG. 3 shows restriction enzyme maps of plasmids pF2, pF3 and pF4.

Type cultures IFO3287, IAM12138 and natural culture isolate of *Gluconobacter oxydans* T-100 (FERM BP-4188) were each inoculated into 10 test tubes containing 6 ml of MB medium [D-mannitol (2.5%), polypeptone (0.3%) and yeast extract (0.5%), pH 6.0], and cultured in a test tube shaker at 30° C. for 18 hours to give a seed culture. MB medium (100 ml) was placed in each of ten 500 ml Erlenmeyer flasks, and 3 ml each of the seed culture was inoculated, which was followed by culture at 30° C. for 6 hours. The ten tubes of culture (1 liter) was centrifuged at 4° C., 6000 rpm for 10 min, and the obtained cells were suspended in 30 ml of P1 solution (100 μg/ml ribonuclease A, 10 mM EDTA, 50 mM Tris-HCl buffer, pH 8.0). A P2 solution (30 ml, 1% SDS, 0.2N sodium hydroxide solution) and P3 solution (30 ml, 3M potassium acetate buffer, pH 5.5) were added, and the mixture was centrifuged at 4° C., 13000 rpm for 30 min. The supernatant was centrifuged again under the same conditions, and the supernatant was adsorbed to Quagen column Tip100 (Quagen) equilibrated with QBT solution (15% ethanol, 0.15% Triton X-100, 750 mM sodium chloride, 50 mM MOPS buffer, pH 7.0), and washed twice with 10 ml of QC solution (15% ethanol, 1M sodium chloride, 50 mM MOPS buffer, pH 7.0), which was followed by elution with 10 ml of QF solution (15% ethanol, 1.25M sodium chloride, 50 mM Tris-HCl buffer, pH 8.5). A 0.7 fold amount of isopropanol was added to the eluate, and the mixture was centrifuged at 4° C., 10000 rpm for 30 min. The precipitate was washed with 70% ethanol and dried in vacuo to give a DNA. The obtained DNA was dissolved in 150 µl of TE buffer (1 mM EDTA, 10 mM Tris-HCl buffer, pH 8.0). Using λHindIII molecular weight marker (Behringer Mannheim AG) as an index, these DNA solutions were migrated on 0.8% agarose gel at 100 V for 30 min, and a single band present in the range of from 2 kb to 5 kb, which was stained with ethidium bromide, was cleaved out from the gel, placed in a dialysis tube, and migrated at 100 V for 30 min, after which migrated for 30 seconds upon reversing the flow direction of the current, and the content of the tube was transferred to an eppendorf tube. After extraction twice with water saturated phenol, the aqueous layer was washed with butanol and dehydrated repeatedly until the washing and dehydration concentrated the solution to 500 µl. 3M Sodium acetate (50 µl) and ethanol (1 ml) were added, and the mixture was left standing overnight at −20° C. The solution was centrifuged at 4° C., 14000 rpm for 30 min. The precipitate was washed with 70% ethanol and dried in vacuo. The resulting precipitate was dissolved in TE buffer to give a plasmid solution. The 2.6 kb plasmid derived from Gluconobacter IFO3287 was named pF2, 3.7 kb plasmid derived from IAM12138 was named pF3, and 4.4 kb plasmid derived from natural culture isolate of Gluconobacter T-100 was named pF4 (see FIG. 3).

(2) Construction of shuttle vector of Gluconobacter and *Escherichia coli*

As a drug resistant plasmid containing a replication origin which functions in *Escherichia coli*, pHSG298 (Takara Shuzo) containing kanamycin resistant gene and lacZ gene containing a multicloning site was used.

Figure 4:
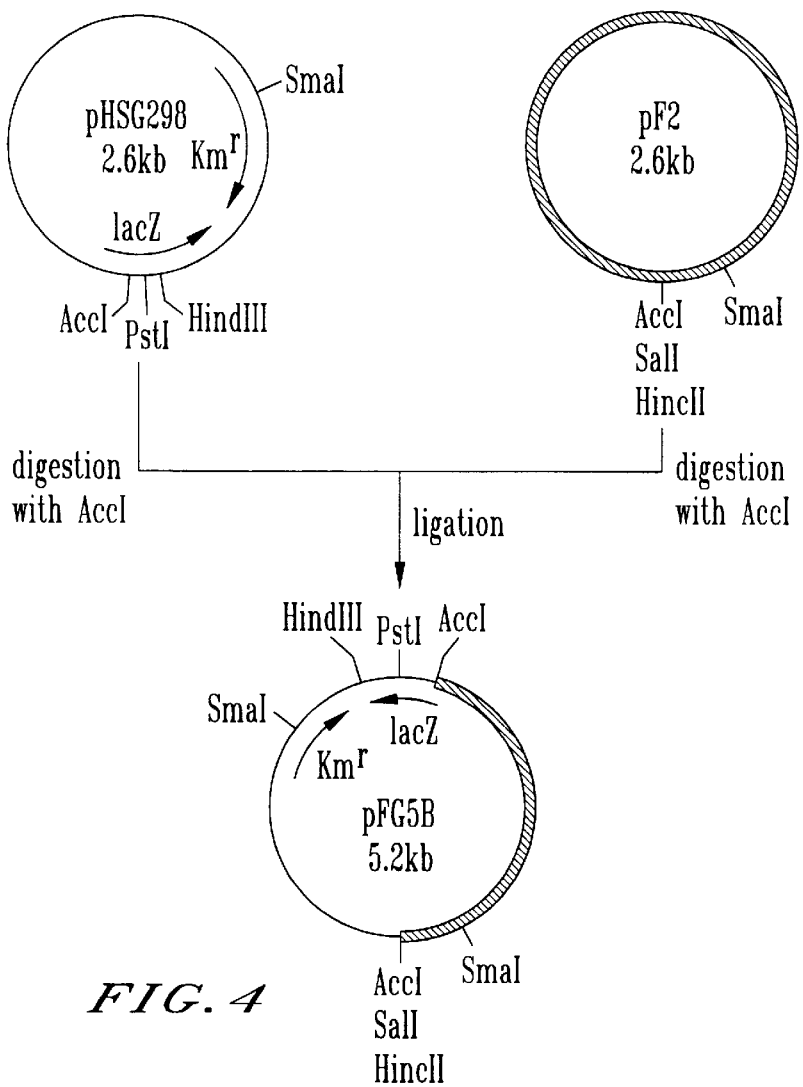
FIG. 4 shows the construction of shuttle vector pFG5B.
Figure 5:
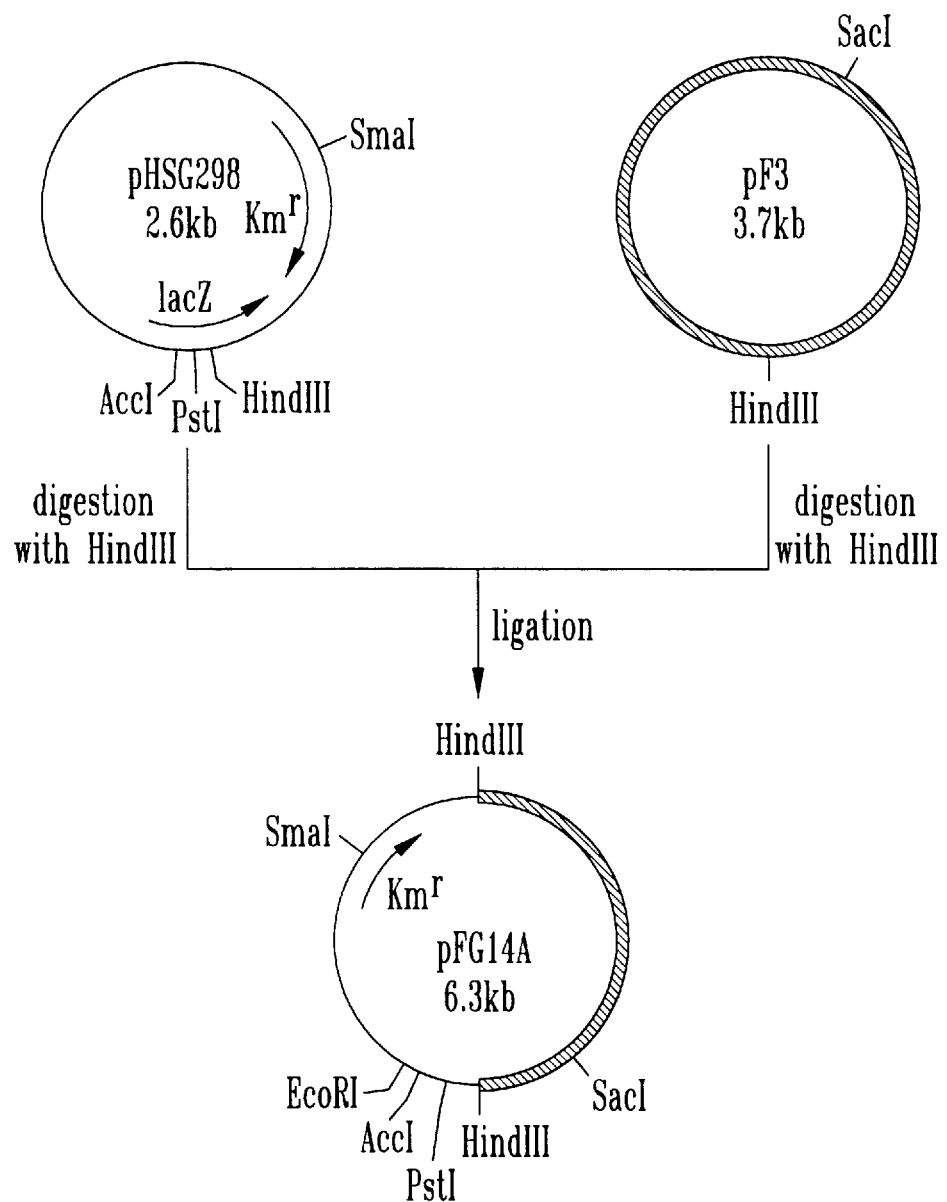
FIG. 5 shows the construction of shuttle vector pFG14A.
Figure 6:
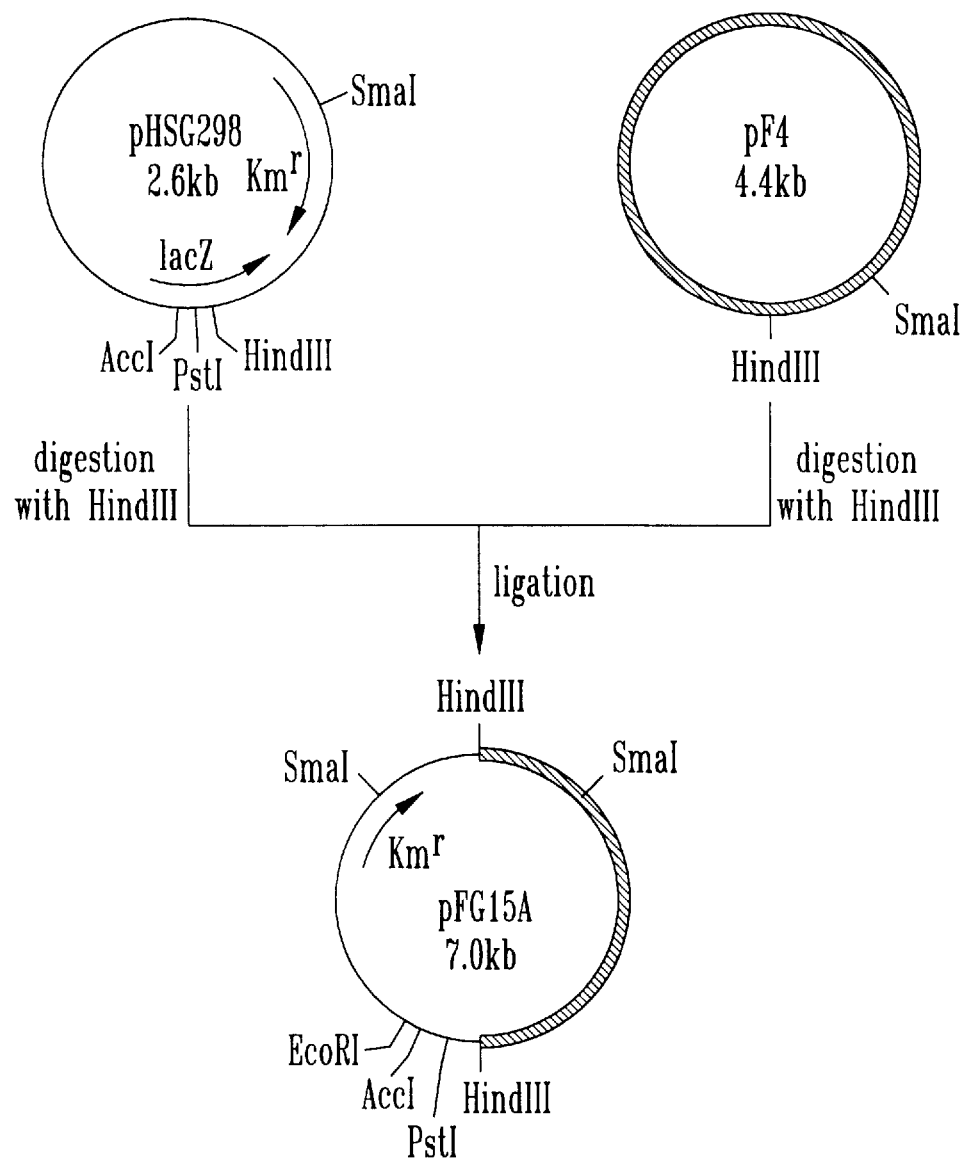
FIG. 6 shows the construction of shuttle vector pFG15A.

The shuttle vector was prepared as in the following. pHSG298 was digested with restriction enzyme AccI (Nippon Gene, Japan), and treated with alkaline phosphatase to give a combined plasmid wherein pF2 digested with AccI was ligated with T4 DNA ligase. This was named pFG5B (see FIG. 4). pHSG298 was partially digested with restriction enzyme HindIII (Nippon Gene, Japan), subjected to alkaline phosphatase treatment, and ligated to pF3 and pF4 digested with HindIII, with the use of T4 DNA ligase. The combined plasmids each carrying a kanamycin resistant gene were named pFG14A and pFG15A (see FIGS. 5 and 6). These combined plasmids were introduced into *E. coli* JM109 by transformation method, and depending on the kanamycin resistance and color development by lacZ, the cell line containing the combined plasmid was selected.

EXAMPLE 13

Transformation of Gluconobacter (1) Preparation of competent cell and transformation

*Gluconobacter oxydans* G624 (FERM BP-4415) was inoculated into a 500 ml Erlenmeyer flask containing 100 ml of a medium containing glucose (2.5%), polypeptone (0.3%) and yeast extract (0.5%), and cultured at 25° C. for about 20 hours. After confirming that the absorbance of the culture at 570 nm was in the range of from 0.6 to 1.2, the cells were collected by centrifugation at 4° C., 6000 rpm for 10 min. The cells were transformed by the electroporation method [Dower, W. J., Miller, J. F. and Ragsdale, C. W., Nucleic Acid Res. Vol. 16, p. 6127 (1988)] according to the case of *E. coli*. The competent cells were collected by washing the above-mentioned centrifuged cells with 10% glycerol and again centrifuging at 4° C., 6000 rpm for 10 min, which was followed by preparation of a suspension of $10^{10}$ cells/ml under microscopy. As the plasmid to be used for transformation, the shuttle vector pFG14A obtained in Example 12-(2) was isolated and purified according to the method of Example 12-(1) and prepared into a solution of DNA 4 mg/ml with TE buffer. The shuttle vector (1 µl) was added to the competent cell suspension (160 µl), mixed, and this transformation solution (60 µl) was placed in a cuvette of Gene Pulser (Bio Rad). Electroporation was carried out at cuvette width 0.1 cm, resistance 200 Ω, voltage 1.8 KV and capacitance 25 µF. MB medium (1 ml) was added to the transformation solution in the cuvette to give a suspension and the entire amount thereof was transferred into a 15 ml Corning tube, which was followed by rotary (80 rpm) incubation in an incubator warm water tank at 30° C. for 2 hours. The suspension was plated on an MB agar plate containing kanamycin (100 µg/ml) and the colonies grown were counted. As a result, it was found that Gluconobacter was barely transformed under the above-mentioned conditions.

The culture conditions of *Gluconobacter oxydans* G624 and the conditions of electroporation were investigated from various aspects. As a result, it was found that the use of D-mannitol as a carbon source of the medium resulted in higher transformation efficiency. Electroporation was most efficiently performed under the above-mentioned conditions. That is, using D-mannitol instead of glucose, electroporation was carried out at cuvette width 0.1 cm, resistance 200 Ω, voltage 1.8 KV and capacitance 25 µF to obtain G624-pFG14A efficiently as shown in Table 8.

TABLE 8

| Kind of medium | Number of transformants (cells/µg DNA) |
|---|---|
| Glucose medium | 0 |
| Mannitol medium | 1500 |

Using the shuttle vectors pFG5B and pFG15A, *Gluconobacter oxydans* G624 was transformed in the same manner as above to give transformants G624-pFG5B and G624-pFG15A. From these results, it was clarified that AccI cleavage site of plasmid pF2 of Gluconobacter, and HindIII cleavage site of pF3 and pF4 of Gluconobacter were each located at sites irrelevant to autoreplicatable unit of each plasmid.

(2) Stability of shuttle vector in host

The stability of shuttle vector in host was examined as in the following.

A culture broth was subcultured twice in MB medium without kanamycin, and each resulting broth was plated on an MB agar plate without kanamycin, which was followed by culture at 30° C. for 2 days. The emerged colonies were replicated on an MB agar plate containing kanamycin (50 µg/ml) and an MB agar plate without kanamycin to examine their stability. The stability was calculated from the following formula. The results are shown in Table 9.

$$\text{Stability (\%)} = \frac{\text{number of kanamycin resistant colonies}}{\text{total number of test colonies}} \times 100$$

TABLE 9

Stability of shuttle vector in host

| Shuttle vector | Subculture | Stability (%) |
|---|---|---|
| pFG5B | 1 | 100 |
| | 2 | 100 |
| pFG14A | 1 | 100 |
| | 2 | 100 |
| pFG15A | 1 | 100 |
| | 2 | 100 |

The sorbose productivity of the transformed cell line into which three kinds of pFG shuttle vectors were introduced was the same as the host, and influence on the productivity by the plasmids was not found.

EXAMPLE 14

Construction of expression vector containing SDH and SNDH genes (1) Construction of pSD5-RIBg To reduce the size of the DNA fragment containing SDH gene and SNDH gene to be incorporated into the shuttle vector, about 2 kb from SalI site to BglII site of pUC19SD5 was deleted.

Figure 7:
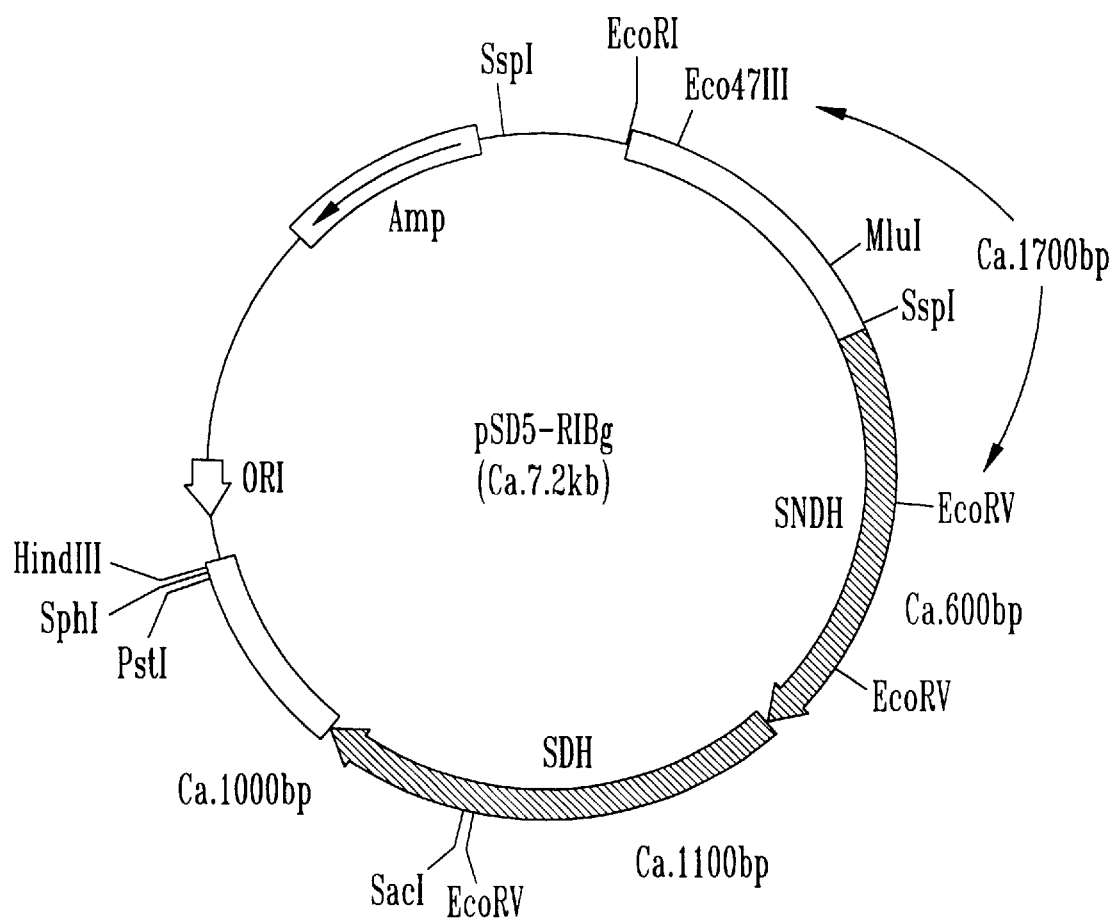
FIG. 7 shows a restriction enzyme map of plasmid pSD5-RIBg.

To be specific, pUC19SD5 was digested with SalI (Nippon Gene, Japan) and BglII (Pharmacia) and the resulting ca. 7,000 and 2,000 DNA fragments were separated by 0.8% agarose electrophoresis. The ca. 7,000 fragment was isolated, DNA end-blunted by DNA polymerase Klenow fragment, and self-ligated with T4 DNA ligase to give plasmid pSD5-RIBg (see FIG. 7).

Figure 8:
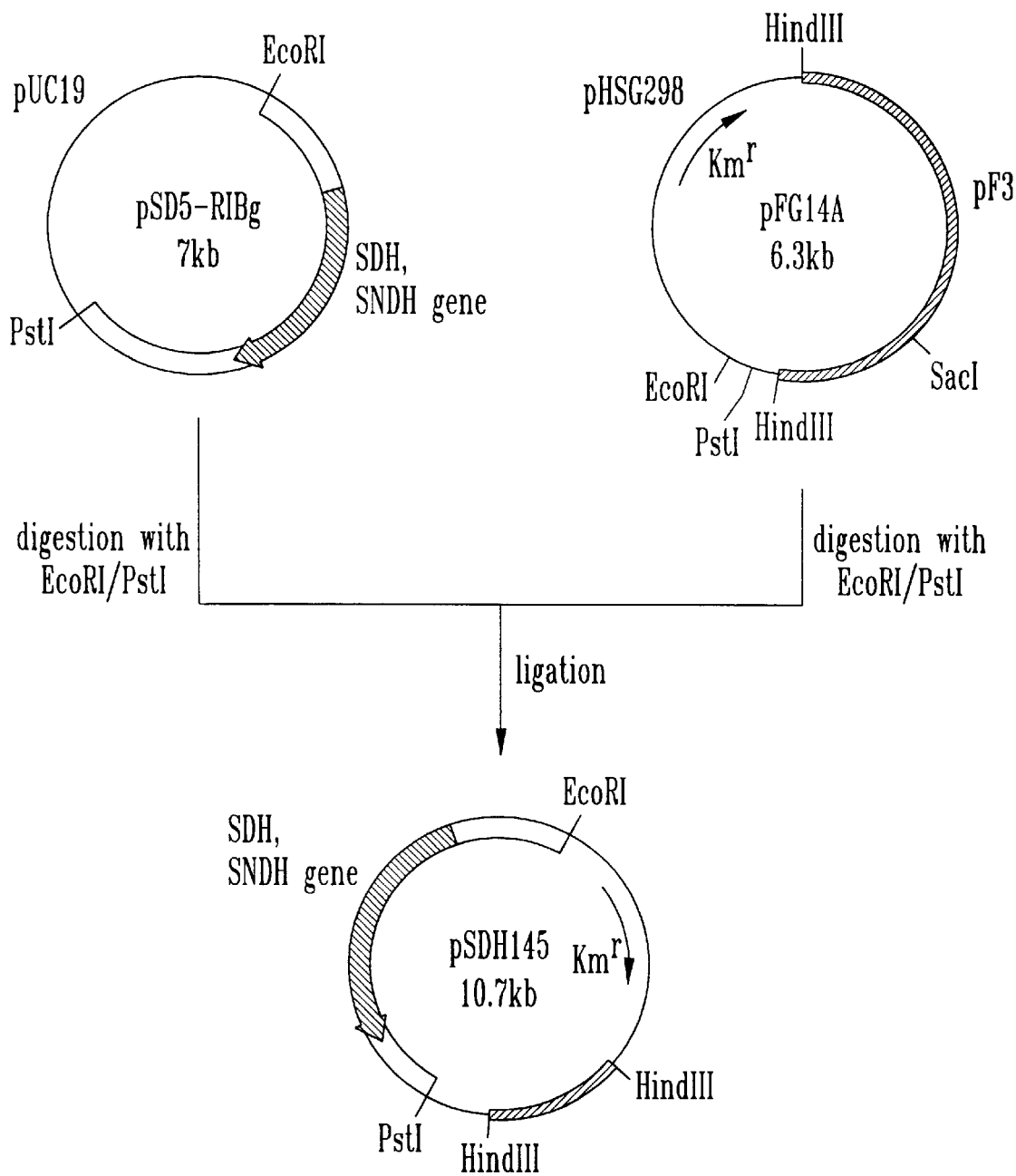
FIG. 8 shows the construction of expression vector pSDH145.
Figure 9:
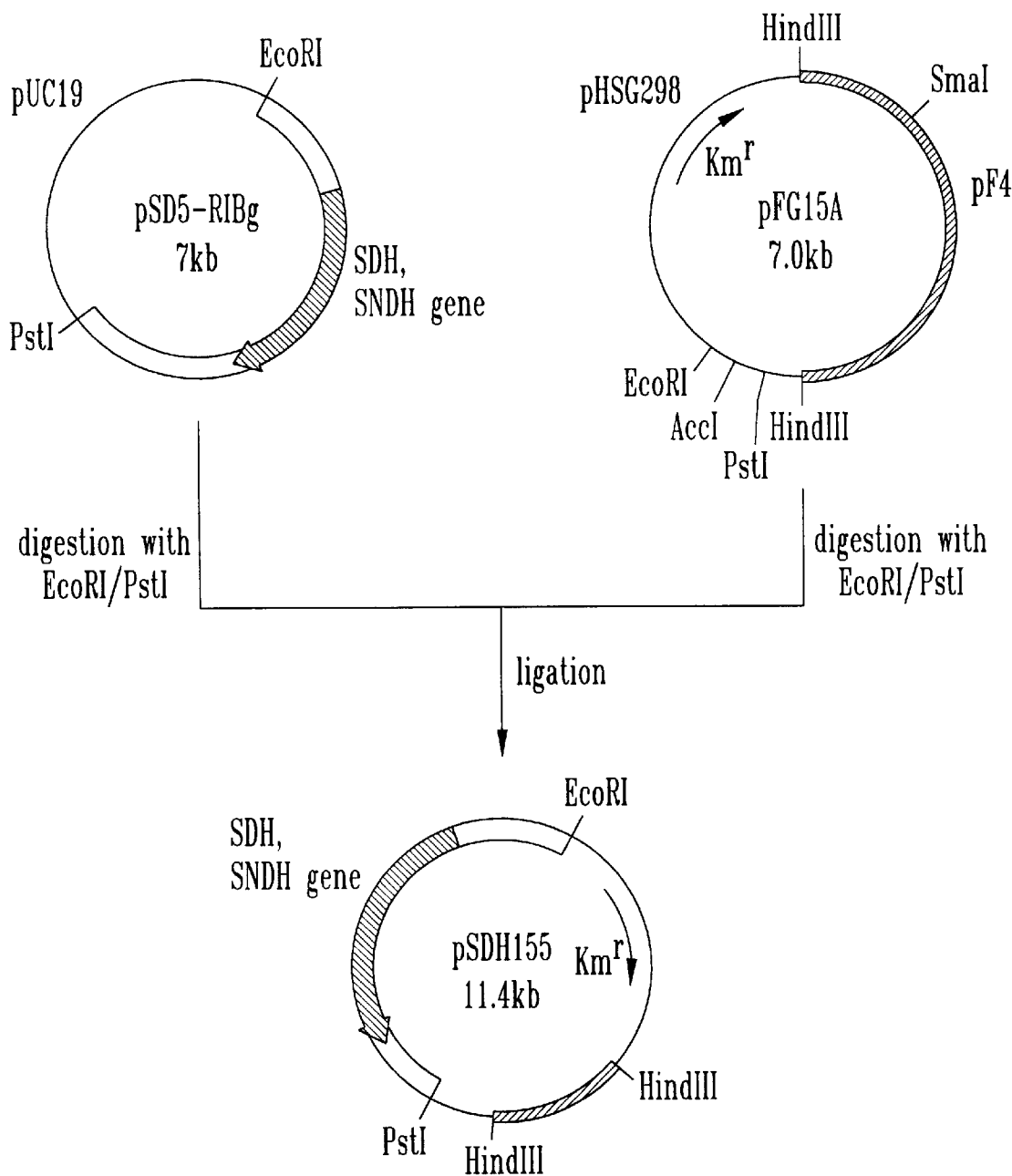
FIG. 9 shows the construction of expression vector pSDH155.

(2) Construction of expression vector pSD5-RIBg was digested with restriction enzymes EcoRI (Nippon Gene, Japan) and PstI (Nippon Gene, Japan) to give ca. 4.4 kb DNA fragment containing SDH gene and SNDH gene. This DNA fragment and the DNA fragment obtained by digesting the shuttle vector pFG14A constructed in Example 12 with restriction enzymes EcoRI and PstI were ligated with T4 DNA ligase to newly construct an expression vector pSDH145 containing SDH and SNDH genes (see FIG. 8). In the same manner, the shuttle vector pFG15A was ligated to construct an expression vector pSDH155 (see FIG. 9).

EXAMPLE 15

DNA Sequence of pSD5-RIBg derived from *Gluconobacter oxydans* T-100

To determine the DNA sequence of 5' upstream region (inclusive of promoter) of SNDH gene and the DNA sequence of 3' downstream region (inclusive of terminator) of SDH gene, pUC19SD5 (FIG. 2) was analyzed by the same method as in Example 5 and Example 9. The results are shown in Sequence Listing SQ:ID No. 5. The promoter region is included in nucleotides 1–1040, SNDH gene and SDH gene are included in nucleotides 1041–4132, and the terminator is included in nucleotide 4133 and the following nucleotides.

EXAMPLE 16

Transformation of *Gluconobacter oxydans* G624 by expression vector (1) Obtaining transformed cell line

*Gluconobacter oxydans* G624 was transformed with the expression vectors pSDH145 and pSDH155 obtained in Example 14 in the same manner as in Example 13 (1) to give transformed cell line G34 (G624-pSDH145) and GA-1 (G624-pSDH155) (FERM BP-4522).

(2) Stability of expression vector in host

Whether or not the expression vectors pSDH145 and pSDH155 are stable in the host *Gluconobacter oxydans* G624 like the shuttle vectors pFG14A and pFG15A, was examined by the method described in Example 13 (2). The results are shown in Table 10.

TABLE 10

Stability of expression vector in host

| Expression vector | Subculture | Stability (%) |
|---|---|---|
| pSDH145 | 1 | 98 |
| | 2 | 93 |
| pSDH155 | 1 | 100 |
| | 2 | 100 |

(3) 2KLGA production by the transformed cell line

The transformed cell line GA-1 was inoculated into a test tube containing 6 ml of a medium containing glucose (2.5%), polypeptone (1.0%), yeast extract (0.5%), calcium carbonate (0.5%) and kanamycin (50 µg/ml), and was cultured in a test tube shaker at 30° C. for 18 hours to give a seed culture. The seed culture (0.3 ml) was inoculated into a 100 ml Erlenmeyer flask containing 10 ml of a medium containing D-sorbitol (5%), yeast extract (0.5%) and calcium carbonate (2.0%). The flask was cultured in a rotary shaker (250 rpm) at 30° C. for 5 days. The obtained culture was centrifuged at 4° C., 6000 rpm for 10 min, and the supernatant was subjected to HPLC analysis described in Example 10-(2) to measure the amount of 2KLGA produced. *Gluconobacter oxydans* T-100 which produces 2KLGA at high yields, which was used for cloning of SDH gene and SNDH gene, was cultured under the same conditions as above, and the amount of 2KLGA produced was measured. The results are shown in Table 11.

TABLE 11

| Cell line | amount of 2KLGA produced (mg/ml) | amount of L-idonic acid prooduced (mg/ml) |
|---|---|---|
| GA-1 | 17 | 12 |
| T-100 | 9 | 7 |

The transformant cell line GA-1 is designed to produce 2KLGA from D-sorbitol, and it is evident that SDH gene and SNDH gene expressed in GA-1 and L-sorbose produced from D-sorbitol by the action of sorbitol dehydrogenase of the host G624 was oxidized by the action of SDH gene and SNDH gene to produce 2KLGA.

Even when compared with *Gluconobacter oxydans* T-100 which is a mutant cell line having an improved 2KLGA production potency and obtained from natural cell line isolate which produces 2KLGA from D-sorbitol, GA-1 showed an appreciably improved production of 2KLGA.

The presence or absence of production of L-idonic acid was examined according to HPLC analysis of 2KLGA described in Example 10-(2), concurrently with the analysis of 2KLGA. The results are shown in Table 11 wherein production of L-idonic acid in a considerable amount by GA-1 is shown. The production route of L-idonic acid is not certain, but blocking of L-idonic acid production route is considered to result in an increased production of 2KLGA.

EXAMPLE 17

Obtaining L-idonic acid low production host
(1) Obtaining L-idonic acid low production transformed cell line The transformed cell line GA-1 was treated with nitrosoguanidine (NTG) to mutate same to give a 2KLGA production cell line *Gluconobacter oxydans* IA1069 having markedly degraded L-idonic acid-producing ability.

According to the method described in Example 16-(3), IA1069 was cultured and 2KLGA and L-idonic acid in the culture were analyzed by HPLC, the results of which are shown in Table 12.

TABLE 12

| Cell line | amount of 2KLGA produced (mg/ml) | amount of L-idonic acid produced (mg/ml) |
|---|---|---|
| IA1069 | 32 | 0 |

(2) Removal of expression vector from L-idonic acid low production transformed cell line IA1069 was treated with novobiocin to remove only the expression vector pSDH155 without affecting production of L-sorbose from D-sorbitol and low production of L-idonic acid The seed culture (1 ml) of IA1069 cultured according to the method of Example 16-(3) was inoculated into a 100 ml Erlenmeyer flask containing 20 ml of MB medium supplemented with novobiocin (0.5 µg/ml), and cultured in a rotary shaker (250 rpm) at 30° C. for 24 hours, which was followed by five times of subculture in the same medium. The obtained culture was plated on an MB agar plate without kanamycin, incubated at 30° C. for 2 days, and the colonies grown were replicated on an MB agar plate without kanamycin and an MB agar plate containing kanamycin (50 µg/ml), and an expression vector pSDH155 deletion cell line was selected. After 5 times of subculture, 50% of the expression vector pSDH155 was found to have been lost. The above-mentioned screening was applied to the expression vector pSDH155 deletion cell line to isolate single cells. According to the method described in Example 12-(1), pSDH155 was confirmed to have been completely removed by agarose electrophoresis. The activity of the obtained expression vector pSDH155 deletion cell line NB6939 to convert D-sorbitol to L-sorbose was investigated according to the method described in Example 11-(1) to find the same level of high sorbose production as *Gluconobacter oxydans* G624.

EXAMPLE 18

Transformation of *Gluconobacter oxydans* NB6939 with expression vector and 2KLGA production of transformed cell line In the same manner as in Example 13-(1), *Gluconobacter oxydans* NB6939 obtained in Example 17 was transformed with the expression vectors pSDH145 and pSDH155 to give transformed cell lines N943 (NB6939-pSDH145) and N952 (NB6939-pSDH155) (FERM BP-4580). With respect to the transformed cell lines N943 and N952, a seed culture (0.3 ml) thereof was each inoculated into a 100 ml flask containing 10 ml of a medium containing D-sorbitol (5%), yeast extract (0.5%) and calcium carbonate (2.0%), in the same manner as in Example 16-(3), and cultured in a rotary shaker (250 rpm) at 30° C. for 7 days.

The obtained culture was centrifuged at 4° C., 6000 rpm for 10 min, and the supernatant was subjected to HPLC to measure the amount of 2KLGA and L-idonic acid produced. The results are shown in Table 13 together with the results of culture of GA-1 concurrently performed.

TABLE 13

| Cell line | amount of 2KLGA produced (mg/ml) | amount of L-idonic acid produced (mg/ml) |
|---|---|---|
| GA-1 | 20 | 16 |
| N943 | 37 | 0 |
| N952 | 38 | 0 |

The results clearly indicate that incorporation of the expression vector in the L-sorbose high producing, 2KLGA low decomposing and L-idonic acid low producing host resulted in noticeable increase of production yield of 2KLGA from D-sorbitol.

EXAMPLE 19

Transformation of *Gluconobacter oxydans* NB6939 with expression vector harboring *E. coli* promoter and 2KLGA production of transformed cell line (1) Construction of expression vector for insertion of promoter The expression vector pSDH155 includes a nucleotide sequence (SQ: ID:No. 5) up to 1040 bp upstream of SNDH translation initiation codon (ATG) of *Gluconobacter oxydans* T-100 chromosomal DNA, and an insertion of a strong promoter sequence in the place of the promoter sequence of SNDH gene is considered to increase expression of SNDH gene and SDH gene. By modifying the nucleotide sequence CCATAG (nucleotides 1017–1022 of SQ:ID No. 5) into NcoI cleavage site (CCATGG) and using this NcoI cleavage site and EcoRI cleavage site of nucleotides 1–6 of SQ:ID No. 5, the promoter sequence can be exchanged.

Figure 10:
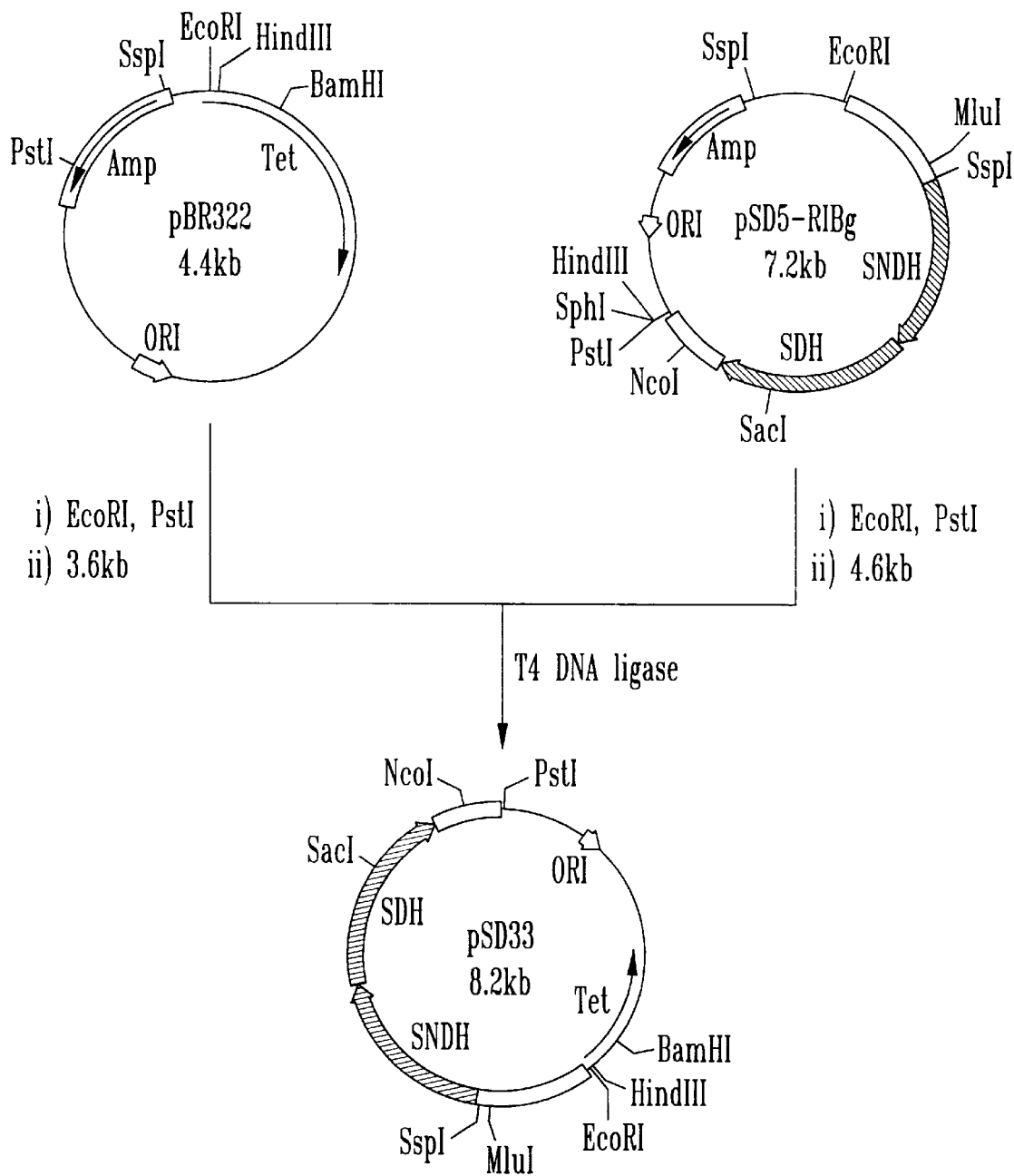
FIG. 10 shows the construction of expression vector pSD33.
Figure 11:
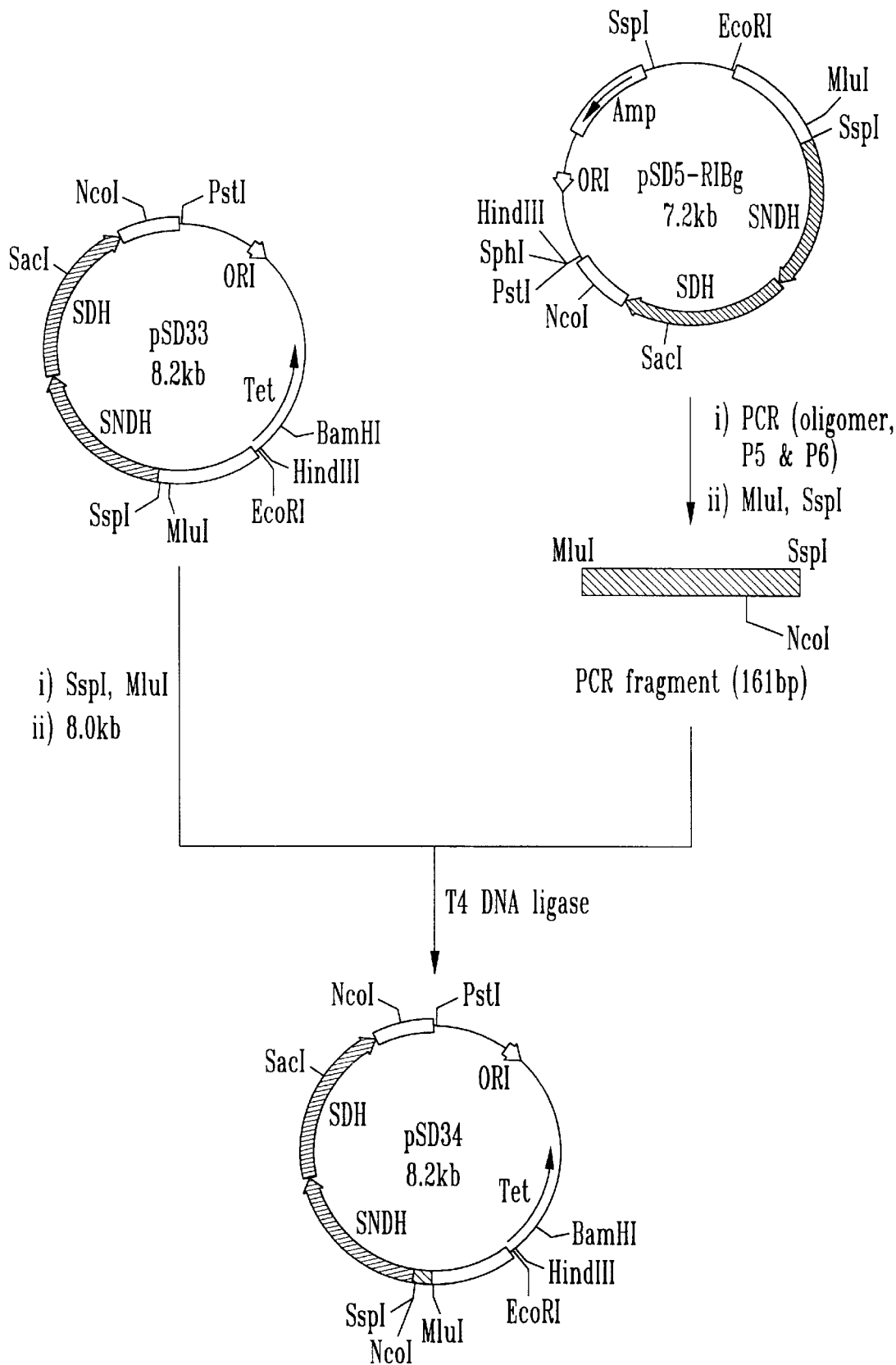
FIG. 11 shows the construction of expression vector pSD34.
Figure 12:
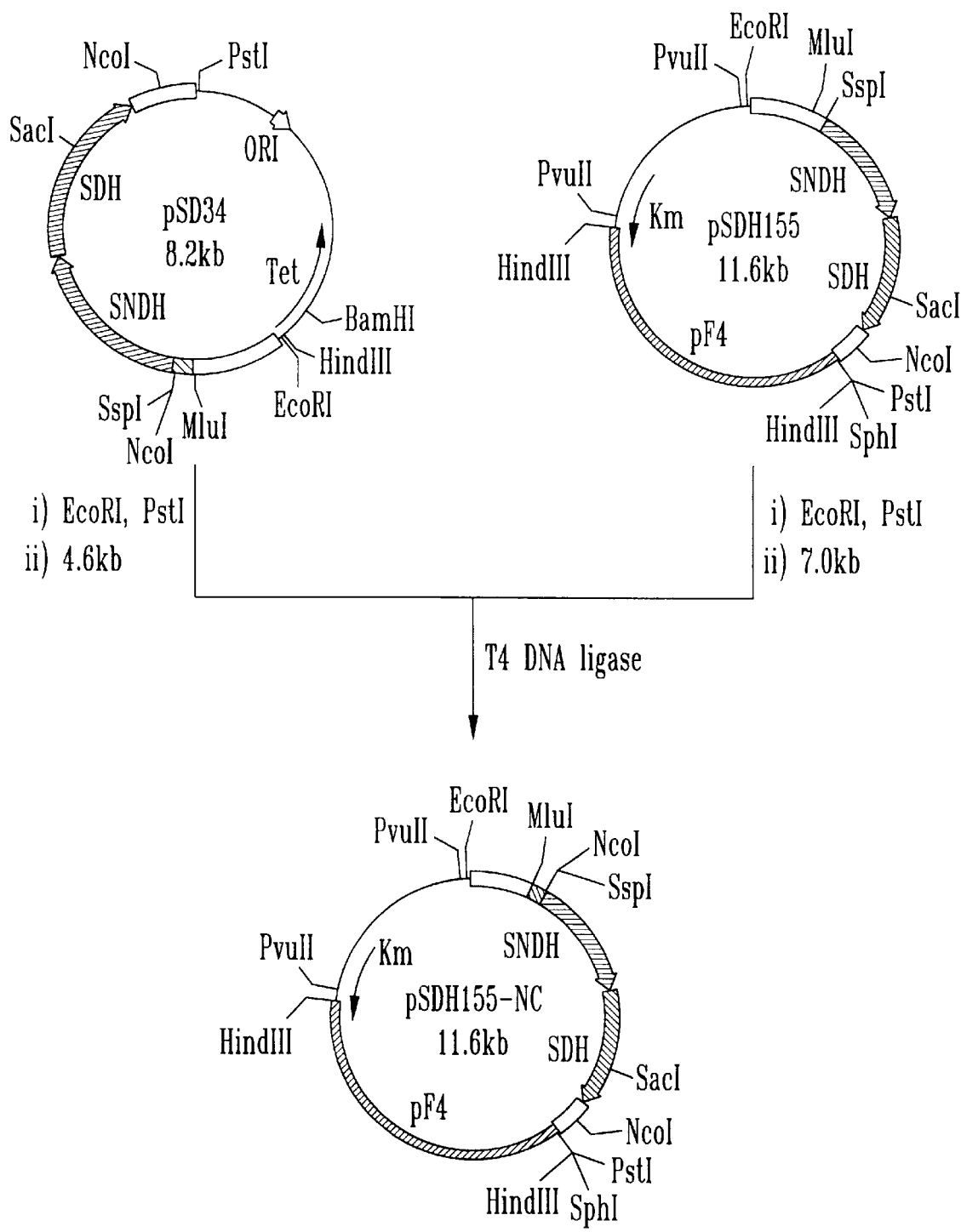
FIG. 12 shows the construction of expression vector pSDH155-NC.
Figure 13:
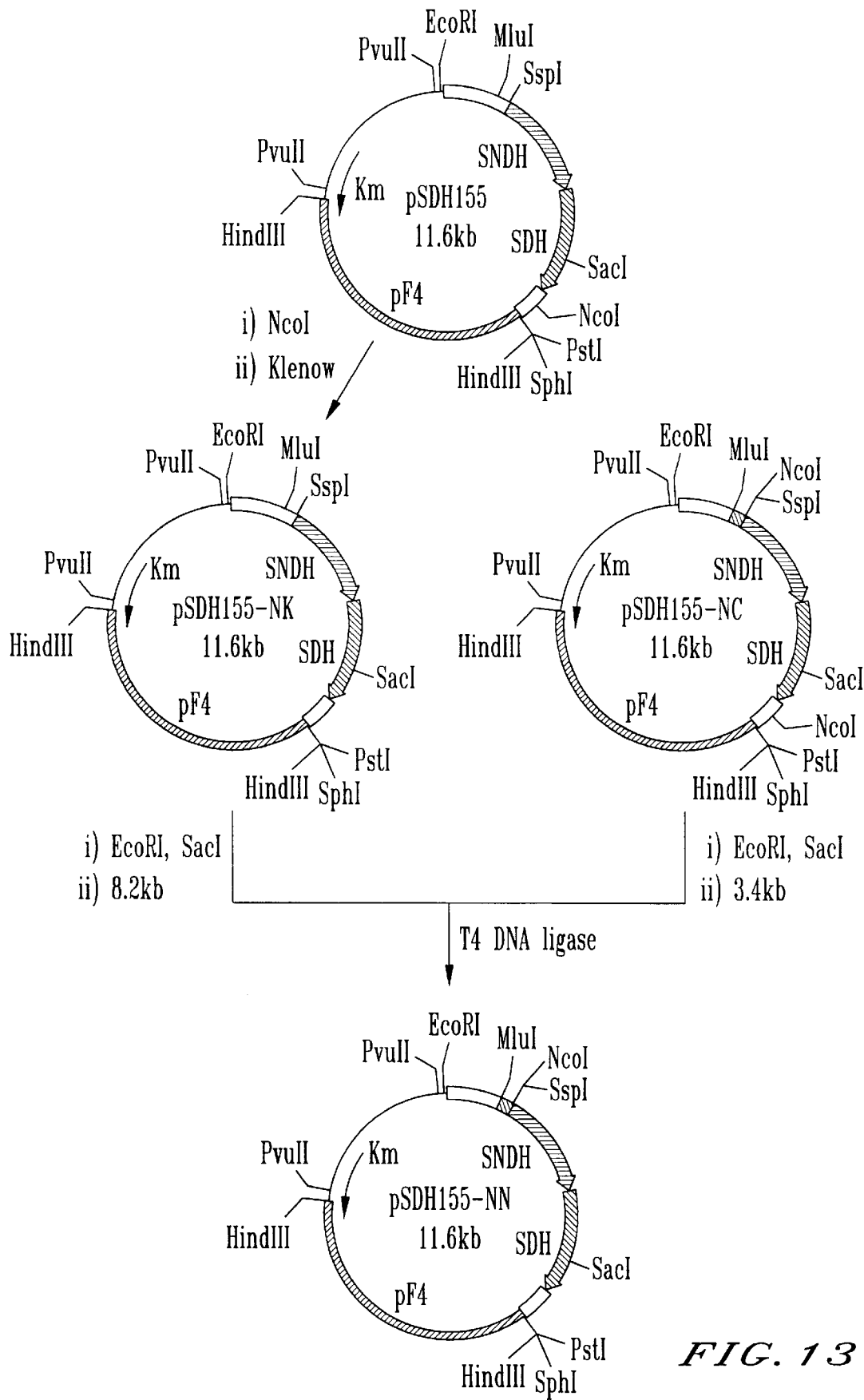
FIG. 13 shows the construction of expression vector pSDH155-NN.

The NcoI cleavage site was introduced into the upstream of the SNDH gene of expression vector pSDH155 to construct an expression vector for inserting a promoter, which does not include NcoI cleavage site in the downstream of SDH gene and lac promoter derived from shuttle vector pFG15A, was constructed.

i) DNA sequence was exchanged by the use of SspI cleavage site (nucleotides 1031–1036 of SQ:ID No. 5) in the upstream of SNDH gene and MluI cleavage site (nucleotides 870–875 of SQ:ID No. 5), and NcoI cleavage site was introduced. pSD5-RIBg (FIG. 7) was digested with EcoRI and PstI, and a ca. 4.6 kb DNA fragment including promoter, SNDH gene and SDH gene was obtained by 0.8% agarose gel electrophoresis. Meanwhile, *E. coli* promoter pBR322 was digested with EcoRI and PstI, and a ca. 3.6 kb DNA fragment including tetracycline resistant gene and replication origin was obtained by 0.8% agarose gel electrophoresis. The both DNA fragments were ligated with T4 DNA ligase to give an *E. coli* expression vector pSD33 including one SspI cleavage site (FIG. 10).

ii) By polymerase chain reaction (PCR), MluI-SspI DNA fragment (nucleotides 870–1036 of SQ:ID No. 5) incorporating an NcoI cleavage site was prepared. To be specific, using pSD5-RIBg as a template, PCR was applied to primer P5 [5' CGG TGC GTT ACG CGT CAG GAAG3', sequence including MluI cleavage site (underline)] and P6 [5' TCA TGA GAA ATA TTC CTA CTG ACC ATG GTG CTG CC3', sequence including SspI cleavage site (underline at 5' side) and NcoI cleavage site (underline at 3' side)](SEQ ID NO:24,25). The PCR product was purified by quick spin column G-25 (Behringer Mannheim AG), digested with SspI and MluI, and MluI-SspI DNA fragment including 161 bp NcoI cleavage site was obtained by 2% agarose gel electrophoresis. Meanwhile, pSD33 was digested with MluI and SspI to isolate a ca. 8.0 kb DNA fragment, and this DNA fragment and the above-mentioned 161 bp MluI-SspI DNA fragment were ligated with T4 DNA ligase to give an E. coli expression vector pSD34 including NcoI cleavage site (FIG. 11)

iii) pSD34 was digested with EcoRI and PstI to isolate a ca. 4.6 kb DNA fragment including SNDH gene upstream sequence including NcoI cleavage site, SNDH gene and SDH gene. Replacement for the corresponding site of expression vector pSDH155 gave expression vector pSDH155-NC having NcoI cleavage site incorporated into the upstream of SNDH gene (FIG. 12).

iv) Since this expression vector pSDH155-NC has one other NcoI cleavage site in the downstream of SDH gene, besides the NcoI cleavage site in the upstream of SNDH gene, the NcoI cleavage site in the downstream of SDH gene was removed (see FIG. 13). Specifically, pSDH155 was digested with NcoI, blunt-ended with DNA polymerase Klenow fragment, and cyclized with T4 DNA ligase to give an expression vector pSDH155-NK without NcoI cleavage site. This pSDH155-NK was digested with EcoRI and SacI to isolate a ca. 8.2 kb DNA fragment wherein the upstream of SNDH gene, SNDH gene and part of SDH gene were deleted. Meanwhile, pSDH155-NC was digested with EcoRI and SacI to isolate a ca. 3.4 kb DNA fragment including the upstream of SNDH gene inclusive of NsoI cleavage site, SNDH gene and part of SDH gene. The both DNA fragments were ligated with T4 DNA ligase to construct an expression vector pSDH155-NN including only one NcoI cleavage site in the upstream of SNDH gene (see FIG. 13).

Figure 14:
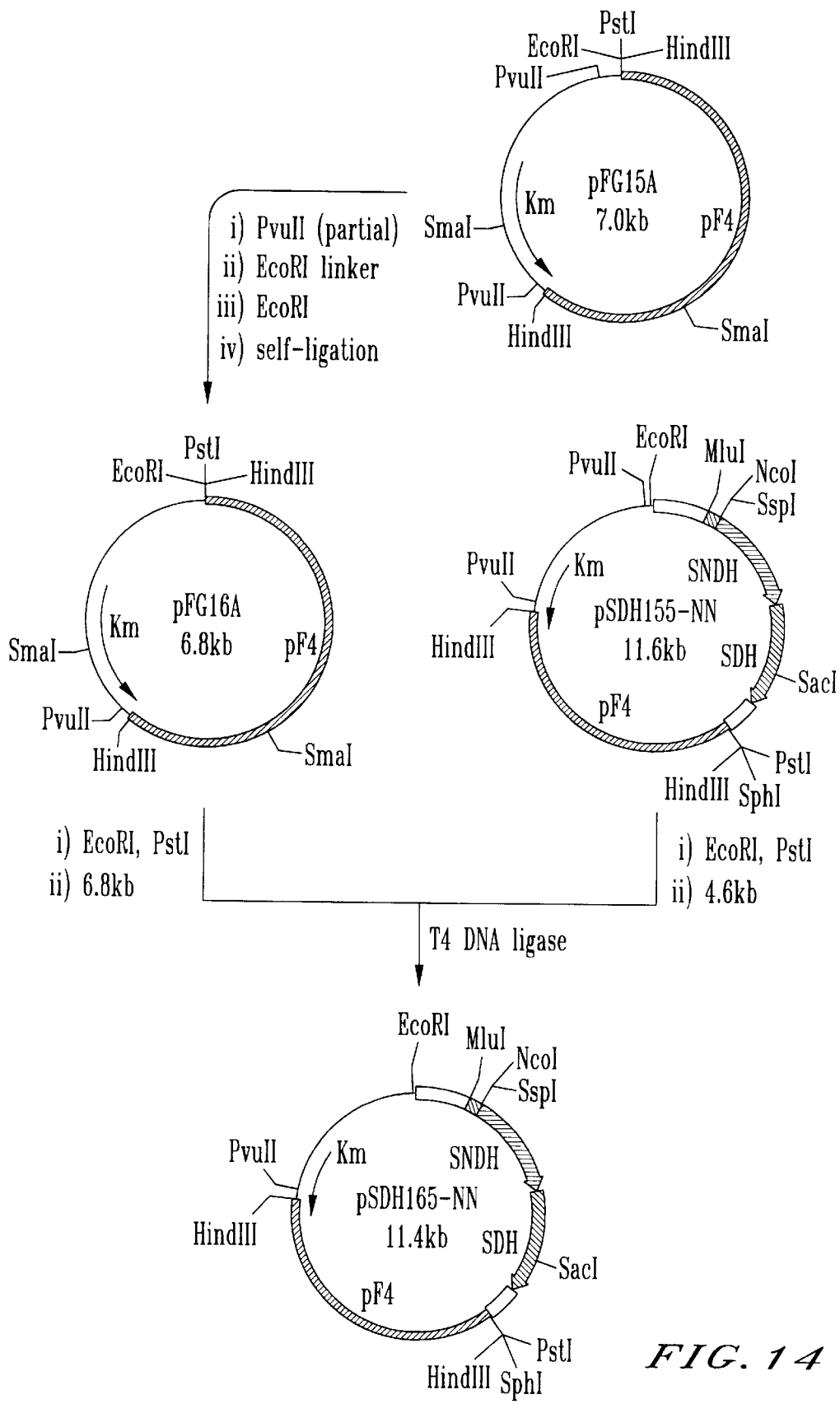
FIG. 14 shows the construction of expression vector pSDH165-NN.

(v) Since this expression vector pSDH155-NN includes lac promoter derived from E. coli plasmid pHSG298, the lac promoter was then removed (FIG. 14). Specifically, shuttle vector pFG15A was partially digested with PvuII to give a ca. 7.0 kb DNA fragment wherein only one PvuII cleavage site was digested. This DNA fragment and EcoRI linker (5' CCG GAA TTC CGG 3') were ligated with T4 DNA ligase, which was followed by heating to inactivate the enzyme (SEQ ID NO:26). Then, the ligated DNA was digested with EcoRI to isolate a ca. 6.8 kb DNA fragment, which was then self-ligated with T4 DNA ligase to give a shuttle vector pFG16A without lac promoter.

This pFG16A was digested with EcoRI and PstI to isolate a ca. 6.8 kb DNA fragment. Meanwhile, pSDH155-NN was digested with EcoRI and PstI to isolate a ca. 4.6 kb DNA fragment including the upstream of SNDH gene inclusive of NcoI cleavage site, SNDH gene and SDH gene. The both DNA fragments were ligated with T4 DNA ligase to give the objective expression vector pSDH165-NN for insertion of promoter (see FIG. 14).

(2) Preparation of DNA oligomers for construction of E. coli promoter

Each E. coli promoter was designed such that an EcoRI cleavage site was ligated with the upstream of −35 region of the promoter and an NcoI cleavage site was ligated with the downstream of −10 region of the promoter. A DNA oligomer constituting the promoter was divided at the middle between the −35 region and −10 region. Four DNA oligomers of DNA oligomer including −35 region, DNA oligomer including −10 region and their complementary DNA oligomers were synthesized using a DNA synthesizer Model 392 (Applied Biosystems). The DNA oligomers constituting each promoter are shown in Table 14.

TABLE 14

DNA oligomers of synthetic E. coli promoters

| name | size | sequence (5' → 3') |
|---|---|---|
| 1. tufB promoter (SEQ ID NO: 27–30) | | |
| TUFB1 | (30) | AAT TCG CAA TTT TTT AGT TGC ATG AAC TCG |
| TUFB2 | (33) | AGA CAT GCG AGT TCA TGC AAC TAA AAA ATT GCG |
| TUFB3 | (29) | CAT GTC TCC ATA GAA TGC GCG CTA CTT GC |
| TUFB4 | (26) | CAT GGC AAG TAG CGC GCA TTC TAT GG |
| 2. trp promoter (SEQ ID NO. 31–34) | | |
| P29 | (30) | AAT TCT GAA ATG AGC TGT TGA CAA TTA ATC |
| P30 | (33) | GTT CGA TGA TTA ATT GTC AAC AGC TCA TTT CAG |
| P31 | (29) | ATC GAA CTA GTT AAC TAG TAC GCA AGT TC |
| P32 | (26) | CAT GGA ACT TGC GTA CTA GTT AAC TA |
| 3. λ PL promoter (SEQ ID NO: 35–38) | | |
| LAMBDA PL1 | (30) | AAT TCT CTC TGG CGG TGT TGA CAT AAA TAC |
| LAMBDA PL2 | (33) | GCC AGT GGT ATT TAT GTC AAC ACC GCC AGA GAG |
| LAMBDA PL3 | (29) | CAC TGG CGG TGA TAC TGA GCA CAT CAG CC |
| LAMBDA PL4 | (26) | CAT GGG CTG ATG TGC TCA GTA TCA CC |
| 4. lac UV-5 promoter (SEQ IDNO: 39–42) | | |
| LAC UV5-1 | (30) | AAT TCG GCA CCC CAG GCT TTA CAC TTT ATG |
| LAC UV5-2 | (35) | AGC CGG AAG CAT AAA GTG TAA AGC CTG GGG TGC CG |
| LAC UV5-3 | (30) | CTT CCG GCT CGT ATA ATG TGT GGA ATT GTC |
| TAC4 | (25) | CAT GGA CAA TTC CAC ACA TTA TAC G |
| 5. lpp promoter (SEQ ID NO: 43–46) | | |
| LPP1 | (30) | AAT TCA TCA AAA AAA TAT TCT CAA CAT AAA |
| LPP2 | (33) | AAA GTT TTT TAT GTT GAG AAT ATT TTT TTG ATG |
| LPP3 | (29) | AAA CTT TGT GTA ATA CTT GTA ACG CTA CC |
| LPP4 | (26) | CAT GGG TAG CGT TAC AAG TAT TAC AC |

TABLE 14-continued

DNA oligomers of synthetic E. coli promoters

| name | size | sequence (5' → 3') |
|---|---|---|
| 6. tac promoter (SEQ ID NO: 31, 47, 48, 42) | | |
| P29 | (30) | AAT TCT GAA ATG AGC TGT TGA CAA TTA ATC |
| TAC2 | (33) | AGC CGA TGA TTA ATT GTC AAC AGC TCA TTT CAG |
| TAC3 | (28) | ATC GGC TCG TAT AAT GTG TGG AAT TGT C |
| TAC4 | (25) | CAT GGA CAA TTC CAC ACA TTA TAC G |

Figure 15:
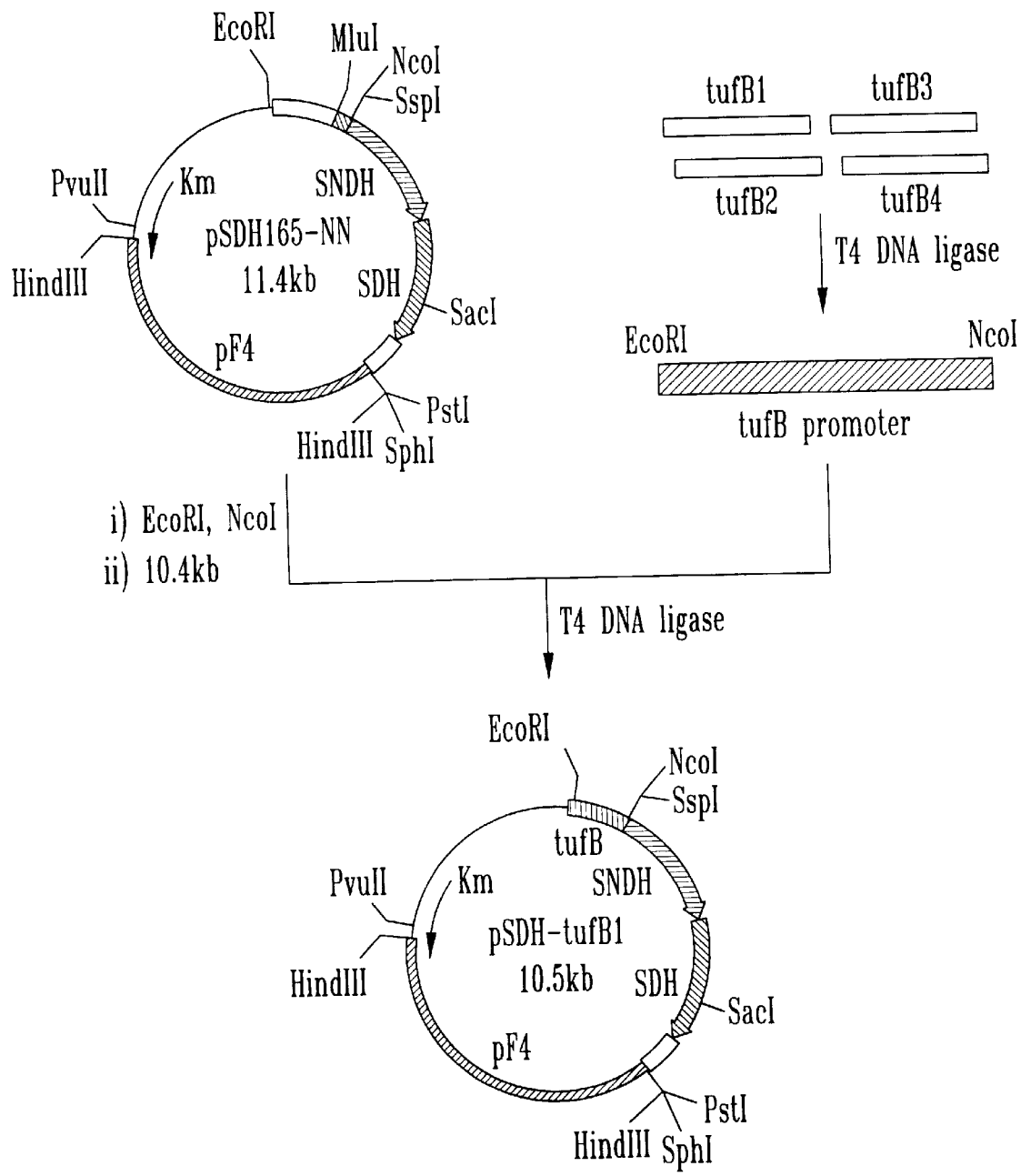
FIG. 15 shows the construction of expression vector pSDH-tufB1.

(3) Construction of expression vector into which E. coli promoter sequence is incorporated An expression vector pSDH-tufB1, into which a tufB promoter sequence was incorporated, was constructed as follows (FIG. 15).

A mixture of DNA oligomers TUFB2 and TUFB3 (1 µl each, approximately 40 pmol), phosphorylation buffer at 10-fold concentration [2 µl, 660 mM Tris-HCl (pH 7.5), 100 mM MgCl$_2$, 150 mM DTT], 10 mM ATP (2 µl), distilled water (12 µl) and T4 polynucleotide kinase (2 µl, 20 units) was incubated at 37° C. for 1 hour and heated at 65° C. for 30 min to inactivate the enzyme. DNA oligomers TUFB1 and TUFB4 (1 µl each, approximately 40 pmol), T4 DNA ligase buffer at 5-fold concentration [8 µl, 250 mM Tris-HCl (pH 7.6), 50 mM MgCl$_2$, 5 mM DTT, 25% PEG-6000], 10 mM ATP (2 µl) and distilled water (4 µl) were added to the reaction mixture (20 µl). The mixture was heated at 70° C. for 5 min and cooled to 4° C. over 30 min. The obtained reaction mixture was added with T4 DNA ligase (2 µl, 600 units, Takara Shuzo) and 10 mM ATP (4 µl), and the mixture was left standing at 16° C. for 2 hours, which was followed by heating at 65° C. for 30 min to inactivate the enzyme. pSDH165-NN was digested with EcoRI and NcoI, and a ca. 10.4 kb DNA fragment was collected. The ligation mixture (1 µl) of oligomers, T4 DNA ligase buffer at 10-fold concentration (2 µl), distilled water (10 µl), 10 mM ATP (2 µl) and T4 DNA ligase (2 µl, 600 units) were added to the resulting DNA fragment (5 µl, 200 ng), and the ligation reaction was performed at 16° C. for 2 hours to give the objective expression vector pSDH-tufB1 (see FIG. 15).

Expression vectors pSDH-trp6 harboring a trp promoter sequence, pSDH-PL1 harboring a λPL promoter sequence, pSDH-lacUV5-2 harboring a lacUV5 promoter sequence, pSDH-lpp1 harboring a lpp promoter sequence and pSDH-tac8 harboring a tac promoter sequence were respectively prepared in the same manner as in the above-mentioned pSDH-tufB1, using DNA oligomers p29, p30, p31 and p32 in Table 14, DNA oligomers LAMBDA PL1, LAMBDA PL2, LAMBDA PL3 and LAMBDA PL4 in Table 14, DNA oligomers LAC UV5-1, LAC UV5-2, LAC UV5-3 and TAC-4 in Table 14, DNA oligomers LPP1, LPP2, LPP3 and LPP4 in Table 14 and DNA oligomers P29, TAC2, TAC3 and TAC4.

(4) Transformation of Gluconobacter oxydans NB6939 with expression vector harboring E. coli promoter and production of 2KLGA by the transformed cell line In the same manner as in Example 13-(1), a host having low productivity of L-idonic acid NB6939 obtained in Example 17 was transformed with the expression vectors harboring an E. coli promoter obtained in Example 19-(3) to give transformed cell lines NB6939-pSDH-tufB1, NB6939-pSDH-trp6, NB6939-pSDH-PL1, NB6939-pSDH-lacUV5-2, NB6939-pSDH-lpp1 and NB6939-pSDH-tac8.

NB6939-pSDH-tufB1, NB6939-pSDH-trp6 and NB6939-pSDH-PL1 were cultured according to the method described in Example 16-(3) to give seed cultures, and 3 ml of these seed cultures was inoculated into 100 ml Erlenmeyer flask containing 10 ml of a medium comprising 10% D-sorbitol, 1.0% corn steep liquor and 2.0% calcium carbonate, and cultured at 32° C. for 5 days in a rotary shaker (250 rpm). The culture was centrifuged at 4° C., 6000 rpm for 10 min, and the supernatant was subjected to HPLC to determine the amount of 2KLGA produced. The results are shown in Table 15 together with the results of the simultaneously performed culture of N952 (NB6939-pSDH155) and NB6939-pSDH165-NN.

TABLE 15

| Cell line | amount of 2KLGA produced (mg/ml) |
|---|---|
| N952 | 52 |
| NB6939-pSDH165-NN | 42 |
| NB6939-PSDH-tufB1 | 75 |
| NB6939-PSDH-trp6 | 73 |
| NB6939-pSDH-PL1 | 73 |

NB6939-pSDH-tufB1, NB6939-pSDH-lac UV5-2, NB6939-pSDH-lpp1 and NB6939-pSDH-tac8 were cultured according to the method described in Example 16-(3) to give seed cultures, and 3 ml of these seed cultures were inoculated into 100 ml Erlenmeyer flask containing 10 ml of a medium comprising 10% D-sorbitol, 1.5% corn steep liquor, 0.15% magnesium sulfate and 2.0% calcium carbonate, and cultured at 32° C. for 5 days in a rotary shaker (250 rpm). The culture was centrifuged at 4° C., 6000 rpm for 10 min, and the supernatant was subjected to HPLC to determine the amount of 2KLGA produced. The results are shown in Table 16 together with the simultaneously performed results of the culture of N952 (NB6939-pSDH155) and NB6939-pSDH165-NN.

TABLE 16

| Cell line | amount of 2KLGA produced (mg/ml) |
|---|---|
| N952 | 73 |
| NB6939-pSDH165-NN | 56 |
| NB6939-pSDH-tufB1 | 91 |
| NB6939-pSDH-lacUV5-2 | 61 |
| NB6939-pSDH-lpp1 | 33 |
| NB6939-pSDH-tac8 | 85 |

What is claimed is:

1. An expression vector comprising: (a) a DNA encoding an L-sorbose dehydrogenase and having the nucleotide sequence of SEQ ID NO: 3, and (b) a DNA encoding an L-sorbosone dehydrogenase and having the nucleotide sequence of SEQ ID NO: 4.

2. A transformant which produces a 2-keto-L-gulonic acid from D-sorbitol, which is obtained by transforming a host microorganism capable of producing L-sorbose at high yields from D-sorbitol, which has no or low 2-keto-L-gulonic acid-decomposing activity, with the expression vector of claim 1.

3. A transformant which produces a 2-keto-L-gulonic acid from D-sorbitol, which is obtained by transforming a host microorganism capable of producing L-sorbose at high yields from D-sorbitol, which has no or low 2-keto-L-gulonic acid-decomposing activity and no or low L-idonic acid producing activity, with the expression vector of claim 1.

4. A biologically pure culture of *Gluconobacter oxydans* G624.

5. *Gluconobacter oxydans* NB6939.

6. A process for producing a 2-keto-L-gulonic acid, comprising culturing the transformant of claim 2 in a medium containing D-sorbitol, and harvesting the 2-keto-L-gulonic acid from the obtained culture.

7. The transformant of claim 2, which is *Gluconobacter oxydans* GA-1 (FERM BP-4522).

8. The transformant of claim 3, which is *Gluconobacter oxydans* N952 (FERM BP-4580).

9. A process for producing a 2-keto-L-gulonic acid, comprising: culturing the transformant of claim 3 in a medium containing D-sorbitol, and harvesting the 2-keto-L-gulonic acid from the obtained culture.

10. A host microorganism transformed by the vector of claim 1.

* * * * *